United States Patent
Kim et al.

(10) Patent No.: US 10,450,600 B2
(45) Date of Patent: Oct. 22, 2019

(54) METHOD OF DESIGNING DNA PROBE CHIP FOR ROOM TEMPERATURE HYBRIDIZATION AND THE DNA PROBE CHIP

(75) Inventors: Tae Sun Kim, Chuncheon-si (KR); Keum Soo Song, Chuncheon-si (KR); Woon Yong Eoum, Chuncheon-si (KR); Chan Young Jung, Chuncheon-si (KR)

(73) Assignee: BIOMETRIX TECHNOLOGY INC., Chuncheon-si (KR)

( * ) Notice: Subject to any disclaimer, the term of this patent is extended or adjusted under 35 U.S.C. 154(b) by 745 days.

(21) Appl. No.: 12/267,421

(22) Filed: Nov. 7, 2008

(65) Prior Publication Data

US 2009/0203005 A1 Aug. 13, 2009

(30) Foreign Application Priority Data

Nov. 19, 2007 (KR) .................. 10-2007-0117736
Sep. 24, 2008 (KR) .................. 10-2008-0093800

(51) Int. Cl.
*C12Q 1/68* (2018.01)
*C12Q 1/6837* (2018.01)

(52) U.S. Cl.
CPC ... *C12Q 1/6837* (2013.01); *B01J 2219/00527* (2013.01); *B01J 2219/00596* (2013.01); *B01J 2219/00612* (2013.01); *B01J 2219/00626* (2013.01); *B01J 2219/00637* (2013.01); *B01J 2219/00659* (2013.01); *B01J 2219/00722* (2013.01)

(58) Field of Classification Search
None
See application file for complete search history.

(56) References Cited

U.S. PATENT DOCUMENTS

| | | | |
|---|---|---|---|
| 6,350,618 B1 * | 2/2002 | Borrelli et al. | 436/174 |
| 7,670,774 B2 * | 3/2010 | Moon | C12Q 1/708 435/283.1 |
| 8,013,188 B2 | 9/2011 | Kim et al. | |
| 8,501,996 B2 | 8/2013 | Kim et al. | |
| 2002/0094528 A1 * | 7/2002 | Salafsky | B82Y 30/00 435/6.11 |
| 2002/0177127 A1 * | 11/2002 | Yang et al. | 435/6 |
| 2002/0187476 A1 * | 12/2002 | Koroulis | C12Q 1/6813 435/6.11 |
| 2008/0194798 A1 | 8/2008 | Kim et al. | |
| 2008/0305477 A1 | 12/2008 | Kim et al. | |
| 2009/0191554 A1 | 7/2009 | Kim et al. | |

FOREIGN PATENT DOCUMENTS

| | | |
|---|---|---|
| KR | 2002-0031734 A | 5/2002 |
| KR | 2004-0078506 A | 10/2004 |
| KR | 2007-0040861 A | 4/2007 |
| KR | 2007-0048353 A | 5/2007 |
| KR | 2007-0052972 A | 5/2007 |
| KR | 2007-0116377 A | 12/2007 |
| KR | 2008-0087292 A | 10/2008 |
| KR | 10-0883763 B1 | 2/2009 |

OTHER PUBLICATIONS

"Viruses" (Wikipedia.com, accessed Nov. 24, 2012).*
"HPV Strains", hpv.org.nz; accessed Oct. 30, 2018, pp. 1-3. (Year: 2018).*
PCT International Search Report for PCT Patent Application No. PCT/KR2008/005721, dated Mar. 31, 2009, 6 pages.
PCT Written Opinion of the International Searching Authority for PCT Patent Application No. PCT/KR2008/005721, dated Mar. 31, 2009, 6 pages.

* cited by examiner

*Primary Examiner* — Bradley L. Sisson
(74) *Attorney, Agent, or Firm* — Womble Bond Dickinson (US) LLP

(57) ABSTRACT

The present invention relates to a method of designing DNA probe chip for room-temperature hybridization in order to solve the solvent evaporation problem occurring when carrying out said hybridization at a high temperature of 40° C.~50° C. or higher, wherein the method is designed to allow genotyping through hybridizing at a room temperature of 20° C.~30° C. The method of designing DNA probe chip comprises designing DNA probe to start at −10~+5 position that is between −10 position which is overlapped 10 sequences with primer and +5 position which is 5 sequences far from the 3'-terminal of primer, based on 0 position which is 3'-terminal of primer.

4 Claims, 38 Drawing Sheets

Specification includes a Sequence Listing.

X = the same as the functional groups representing the connecting parts having aldehyde terminal groups of formula 1 amine slide glass

III monolayer of aminocalixarene derivative
or iminecalixarene derivative

Probe Length   Effective Tm        Probe Length   Effective Tm
16(13mer, 27°C)     ○○ ○○○       18(11mer, 27°C)
16(15mer, 31°C)     ○○   ○○       18(13mer, 33°C)
16(17mer, 37°C)     ○○   ○○       18(15mer, 39°C)
16(19mer, 41°C)     ○○   ○○       18(17mer, 45°C)
16(21mer, 47°C)     ○○   ○○       18(19mer, 51°C)
16(23mer, 55°C)     ○○ ○○○       18(21mer, 57°C)
Room-Temperature Hybridization
for 30 Minutes
P.G=60
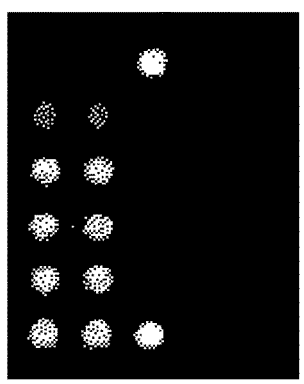
T16
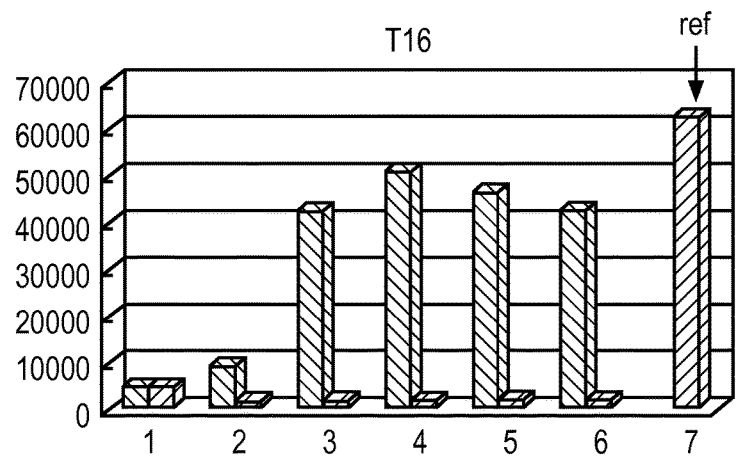
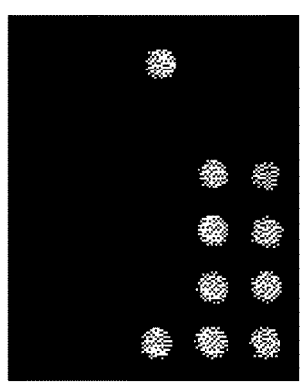
T18
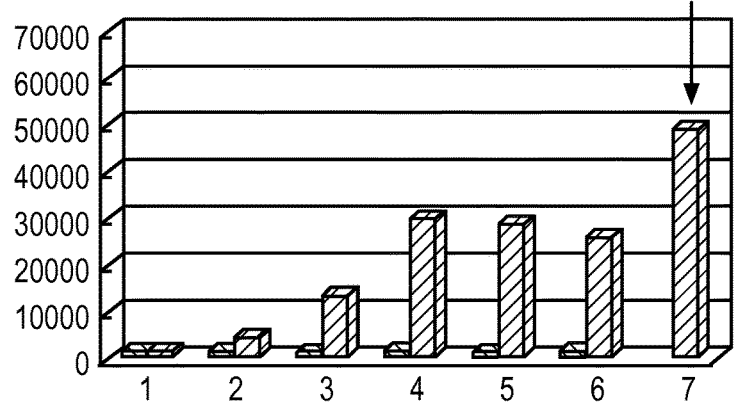
FIG. 3B-1

HPV 16

HPV 18

HPV 6

HPV 11

HPV 31

HPV 33

HPV 35

HPV 35

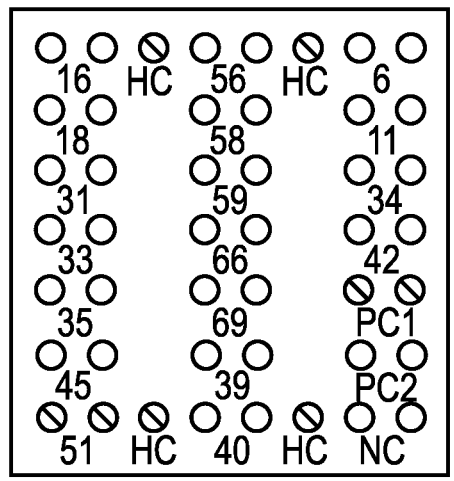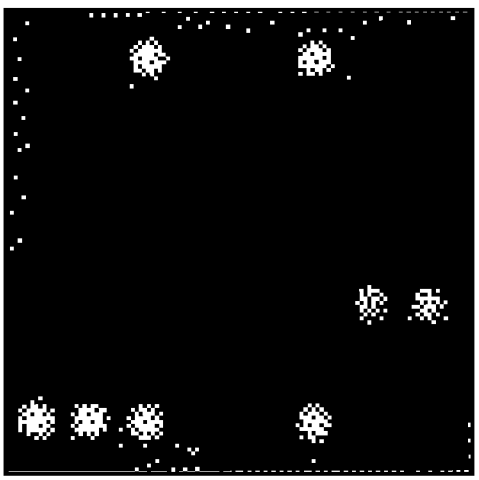
HPV 51
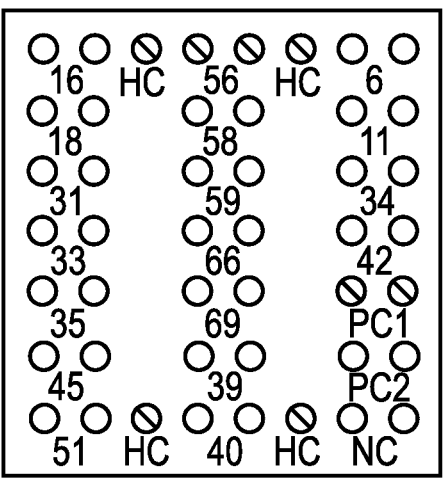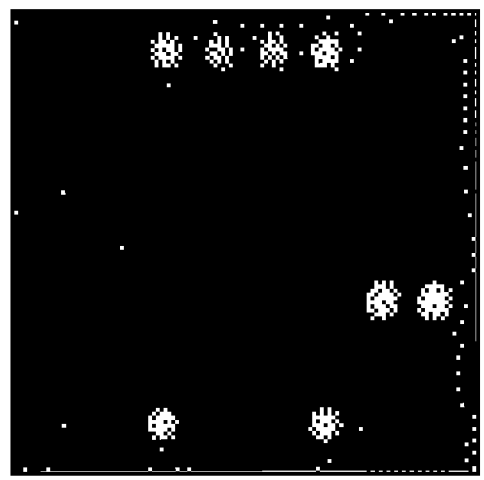
HPV 56
FIG. 7C-1 (Continued)

[도7k] HPV 58

[도7k] HPV 59

HPV 66

HPV 68

HPV 34

HPV 42

NC

SEQUENCE LISTING

<160> NUMBER OF SEQ ID NOS: 65

<210> SEQ ID NO 1
<211> LENGTH: 22
<212> TYPE: DNA
<213> ORGANISM: Artificial Sequence
<220> FEATURE:
<223> OTHER INFORMATION: DNA

<400> SEQUENCE: 1 ggggggggggt tattttccta ca                                              22

<210> SEQ ID NO 2
<211> LENGTH: 24
<212> TYPE: DNA
<213> ORGANISM: Artificial Sequence
<220> FEATURE:
<223> OTHER INFORMATION: DNA

<400> SEQUENCE: 2 gggggggggga attattttcc taca                                            24

<210> SEQ ID NO 3
<211> LENGTH: 26
<212> TYPE: DNA
<213> ORGANISM: Artificial Sequence
<220> FEATURE:
<223> OTHER INFORMATION: DNA

<400> SEQUENCE: 3 ggggggggggc aaattatttt cctaca                                          26

<210> SEQ ID NO 4
<211> LENGTH: 28
<212> TYPE: DNA
<213> ORGANISM: Artificial Sequence
<220> FEATURE:
<223> OTHER INFORMATION: DNA

<400> SEQUENCE: 4 ggggggggggt tcaaattatt ttcctaca                                        28

<210> SEQ ID NO 5
<211> LENGTH: 30
<212> TYPE: DNA
<213> ORGANISM: Artificial Sequence
<220> FEATURE:
<223> OTHER INFORMATION: DNA

<400> SEQUENCE: 5 gggggggggga gttcaaatta ttttcctaca                                      30

<210> SEQ ID NO 6
<211> LENGTH: 32
<212> TYPE: DNA
<213> ORGANISM: Artificial Sequence
<220> FEATURE:
<223> OTHER INFORMATION: DNA

<400> SEQUENCE: 6 ggggggggggc cagttcaaat tattttccta ca                                   32

<210> SEQ ID NO 7
<211> LENGTH: 20
<212> TYPE: DNA
<213> ORGANISM: Artificial Sequence

```
<220> FEATURE:
<223> OTHER INFORMATION: DNA

<400> SEQUENCE: 7 gggggggga ttctccctct                                              20

<210> SEQ ID NO 8
<211> LENGTH: 22
<212> TYPE: DNA
<213> ORGANISM: Artificial Sequence
<220> FEATURE:
<223> OTHER INFORMATION: DNA

<400> SEQUENCE: 8 ggggggggg tattctccct ct                                           22

<210> SEQ ID NO 9
<211> LENGTH: 24
<212> TYPE: DNA
<213> ORGANISM: Artificial Sequence
<220> FEATURE:
<223> OTHER INFORMATION: DNA

<400> SEQUENCE: 9 ggggggggg tgtattctcc ctct                                         24

<210> SEQ ID NO 10
<211> LENGTH: 26
<212> TYPE: DNA
<213> ORGANISM: Artificial Sequence
<220> FEATURE:
<223> OTHER INFORMATION: DNA

<400> SEQUENCE: 10 ggggggggg tgtgtattct ccctct                                       26

<210> SEQ ID NO 11
<211> LENGTH: 28
<212> TYPE: DNA
<213> ORGANISM: Artificial Sequence
<220> FEATURE:
<223> OTHER INFORMATION: DNA

<400> SEQUENCE: 11 ggggggggc tgtgtgtatt ctccctct                                     28

<210> SEQ ID NO 12
<211> LENGTH: 30
<212> TYPE: DNA
<213> ORGANISM: Artificial Sequence
<220> FEATURE:
<223> OTHER INFORMATION: DNA

<400> SEQUENCE: 12 gggggggga gctgtgtgta ttctccctct                                   30

<210> SEQ ID NO 13
<211> LENGTH: 27
<212> TYPE: DNA
<213> ORGANISM: Artificial Sequence
<220> FEATURE:
<223> OTHER INFORMATION: forward primer

<400> SEQUENCE: 13
gatggtgata tggtagatac aggattt                                     27
```

<210> SEQ ID NO 14
<211> LENGTH: 29
<212> TYPE: DNA
<213> ORGANISM: Artificial Sequence
<220> FEATURE:
<223> OTHER INFORMATION: cy5-reverse primer

<400> SEQUENCE: 14
cctagtggct ctatggtaac ctctgacgc                             29

<210> SEQ ID NO 15
<211> LENGTH: 28
<212> TYPE: DNA
<213> ORGANISM: Artificial Sequence
<220> FEATURE:
<223> OTHER INFORMATION: DNA

<400> SEQUENCE: 15 ggggggggggt tcaaattatt ttcctaca                             28

<210> SEQ ID NO 16
<211> LENGTH: 28
<212> TYPE: DNA
<213> ORGANISM: Artificial Sequence
<220> FEATURE:
<223> OTHER INFORMATION: DNA

<400> SEQUENCE: 16 ggggggggggc agttcaaatt attttcct                             28

<210> SEQ ID NO 17
<211> LENGTH: 27
<212> TYPE: DNA
<213> ORGANISM: Artificial Sequence
<220> FEATURE:
<223> OTHER INFORMATION: DNA

<400> SEQUENCE: 17
gggggggggg ccagttcaaa ttatttt                               27

<210> SEQ ID NO 18
<211> LENGTH: 27
<212> TYPE: DNA
<213> ORGANISM: Artificial Sequence
<220> FEATURE:
<223> OTHER INFORMATION: DNA

<400> SEQUENCE: 18 ggggggggggt tagccagttc aaattat                              27

<210> SEQ ID NO 19
<211> LENGTH: 27
<212> TYPE: DNA
<213> ORGANISM: Artificial Sequence
<220> FEATURE:
<223> OTHER INFORMATION: DNA

<400> SEQUENCE: 19
ggggggggga atttagccag ttcaaat                               27

<210> SEQ ID NO 20
<211> LENGTH: 26
<212> TYPE: DNA
<213> ORGANISM: Artificial Sequence
<220> FEATURE:
<223> OTHER INFORMATION: DNA

```
<400> SEQUENCE: 20
gggggggggc aaatttagcc agttca                                            26

<210> SEQ ID NO 21
<211> LENGTH: 26
<212> TYPE: DNA
<213> ORGANISM: Artificial Sequence
<220> FEATURE:
<223> OTHER INFORMATION: DNA

<400> SEQUENCE: 21 ggggggggt attttcctac acctag                                             26

<210> SEQ ID NO 22
<211> LENGTH: 29
<212> TYPE: DNA
<213> ORGANISM: Artificial Sequence
<220> FEATURE:
<223> OTHER INFORMATION: DNA

<400> SEQUENCE: 22 ggggggggt attttcctac acctagtgg                                          29

<210> SEQ ID NO 23
<211> LENGTH: 32
<212> TYPE: DNA
<213> ORGANISM: Artificial Sequence
<220> FEATURE:
<223> OTHER INFORMATION: DNA

<400> SEQUENCE: 23 ggggggggt attttcctac acctagtggt tc                                      32

<210> SEQ ID NO 24
<211> LENGTH: 35
<212> TYPE: DNA
<213> ORGANISM: Artificial Sequence
<220> FEATURE:
<223> OTHER INFORMATION: DNA

<400> SEQUENCE: 24 ggggggggt attttcctac acctagtggt tctat                                   35

<210> SEQ ID NO 25
<211> LENGTH: 38
<212> TYPE: DNA
<213> ORGANISM: Artificial Sequence
<220> FEATURE:
<223> OTHER INFORMATION: DNA

<400> SEQUENCE: 25 ggggggggt attttcctac acctagtggt tctatggt                                38

<210> SEQ ID NO 26
<211> LENGTH: 41
<212> TYPE: DNA
<213> ORGANISM: Artificial Sequence
<220> FEATURE:
<223> OTHER INFORMATION: DNA

<400> SEQUENCE: 26 ggggggggt attttcctac acctagtggt tctatggtta c                            41

<210> SEQ ID NO 27
```

<210> SEQ ID NO 27
<211> LENGTH: 44
<212> TYPE: DNA
<213> ORGANISM: Artificial Sequence
<220> FEATURE:
<223> OTHER INFORMATION: DNA

<400> SEQUENCE: 27
gggggggggt attttcctac acctagtggt tctatggtta cctc                    44

<210> SEQ ID NO 28
<211> LENGTH: 47
<212> TYPE: DNA
<213> ORGANISM: Artificial Sequence
<220> FEATURE:
<223> OTHER INFORMATION: DNA

<400> SEQUENCE: 28
gggggggggt attttcctac acctagtggt tctatggtta cctctga                 47

<210> SEQ ID NO 29
<211> LENGTH: 50
<212> TYPE: DNA
<213> ORGANISM: Artificial Sequence
<220> FEATURE:
<223> OTHER INFORMATION: DNA

<400> SEQUENCE: 29
gggggggggt attttcctac acctagtggt tctatggtta cctctgatgc              50

<210> SEQ ID NO 30
<211> LENGTH: 28
<212> TYPE: DNA
<213> ORGANISM: Artificial Sequence
<220> FEATURE:
<223> OTHER INFORMATION: DNA

<400> SEQUENCE: 30
gggggggggt tcaaattatt ttcctaca                                      28

<210> SEQ ID NO 31
<211> LENGTH: 26
<212> TYPE: DNA
<213> ORGANISM: Artificial Sequence
<220> FEATURE:
<223> OTHER INFORMATION: DNA

<400> SEQUENCE: 31
gggggggggg tgtgtattct ccctct                                        26

<210> SEQ ID NO 32
<211> LENGTH: 27
<212> TYPE: DNA
<213> ORGANISM: Artificial Sequence
<220> FEATURE:
<223> OTHER INFORMATION: DNA

<400> SEQUENCE: 32
ggggggggga gtacatactt tcctaca                                       27

<210> SEQ ID NO 33
<211> LENGTH: 26
<212> TYPE: DNA
<213> ORGANISM: Artificial Sequence
<220> FEATURE:
<223> OTHER INFORMATION: DNA

<400> SEQUENCE: 33 ggggggggggg tgctttttttt cccact                                26

<210> SEQ ID NO 34
<211> LENGTH: 28
<212> TYPE: DNA
<213> ORGANISM: Artificial Sequence
<220> FEATURE:
<223> OTHER INFORMATION: DNA

<400> SEQUENCE: 34
gggggggggt actagttatt ttcctact                                28

<210> SEQ ID NO 35
<211> LENGTH: 25
<212> TYPE: DNA
<213> ORGANISM: Artificial Sequence
<220> FEATURE:
<223> OTHER INFORMATION: DNA

<400> SEQUENCE: 35
gggggggggt gtgtattccc cttct                                   25

<210> SEQ ID NO 36
<211> LENGTH: 27
<212> TYPE: DNA
<213> ORGANISM: Artificial Sequence
<220> FEATURE:
<223> OTHER INFORMATION: DNA

<400> SEQUENCE: 36
gggggggggt atatatactc tgctact                                 27

<210> SEQ ID NO 37
<211> LENGTH: 27
<212> TYPE: DNA
<213> ORGANISM: Artificial Sequence
<220> FEATURE:
<223> OTHER INFORMATION: DNA

<400> SEQUENCE: 37 gggggggggga gagaaccccc tccgagt                                27

<210> SEQ ID NO 38
<211> LENGTH: 26
<212> TYPE: DNA
<213> ORGANISM: Artificial Sequence
<220> FEATURE:
<223> OTHER INFORMATION: DNA

<400> SEQUENCE: 38 ggggggggg tgcatttttt ccaact                                   26

<210> SEQ ID NO 39
<211> LENGTH: 29
<212> TYPE: DNA
<213> ORGANISM: Artificial Sequence
<220> FEATURE:
<223> OTHER INFORMATION: DNA

<400> SEQUENCE: 39 ggggggggggc caacccaggc agttattta                              29

<210> SEQ ID NO 40
<211> LENGTH: 25
<212> TYPE: DNA

<213> ORGANISM: Artificial Sequence
<220> FEATURE:
<223> OTHER INFORMATION: DNA

<400> SEQUENCE: 40
gggggggggt cctcccagtt ctgta                                    25

<210> SEQ ID NO 41
<211> LENGTH: 26
<212> TYPE: DNA
<213> ORGANISM: Artificial Sequence
<220> FEATURE:
<223> OTHER INFORMATION: DNA

<400> SEQUENCE: 41
gggggggggg tgtatgcccc ctcgcc                                   26

<210> SEQ ID NO 42
<211> LENGTH: 26
<212> TYPE: DNA
<213> ORGANISM: Artificial Sequence
<220> FEATURE:
<223> OTHER INFORMATION: DNA

<400> SEQUENCE: 42
gggggggggc tgtatactgc ccctct                                   26

<210> SEQ ID NO 43
<211> LENGTH: 30
<212> TYPE: DNA
<213> ORGANISM: Artificial Sequence
<220> FEATURE:
<223> OTHER INFORMATION: DNA

<400> SEQUENCE: 43 gggggggga ggcagtattt attactccac                                30

<210> SEQ ID NO 44
<211> LENGTH: 27
<212> TYPE: DNA
<213> ORGANISM: Artificial Sequence
<220> FEATURE:
<223> OTHER INFORMATION: DNA

<400> SEQUENCE: 44 gggggggga gtatatatgt taacacc                                   27

<210> SEQ ID NO 45
<211> LENGTH: 39
<212> TYPE: DNA
<213> ORGANISM: Artificial Sequence
<220> FEATURE:
<223> OTHER INFORMATION: DNA

<400> SEQUENCE: 45
gggggggggt ctgtagctac tagtatttat gtacataca                     39

<210> SEQ ID NO 46
<211> LENGTH: 26
<212> TYPE: DNA
<213> ORGANISM: Artificial Sequence
<220> FEATURE:
<223> OTHER INFORMATION: DNA

<400> SEQUENCE: 46
gggggggggg tgtgttttat cctact                                   26

<210> SEQ ID NO 47
<211> LENGTH: 32
<212> TYPE: DNA
<213> ORGANISM: Artificial Sequence
<220> FEATURE:
<223> OTHER INFORMATION: DNA

<400> SEQUENCE: 47 ggggggggggc agacataatt taggtagtag ta           32

<210> SEQ ID NO 48
<211> LENGTH: 29
<212> TYPE: DNA
<213> ORGANISM: Artificial Sequence
<220> FEATURE:
<223> OTHER INFORMATION: Positive control

<400> SEQUENCE: 48 ggggggggggt attttcctac acctagtgg              29

<210> SEQ ID NO 49
<211> LENGTH: 29
<212> TYPE: DNA
<213> ORGANISM: Artificial Sequence
<220> FEATURE:
<223> OTHER INFORMATION: Positive control

<400> SEQUENCE: 49 ggggggggggt attctccctc tcctagtgg              29

<210> SEQ ID NO 50
<211> LENGTH: 29
<212> TYPE: DNA
<213> ORGANISM: Artificial Sequence
<220> FEATURE:
<223> OTHER INFORMATION: Positive control

<400> SEQUENCE: 50 ggggggggggt actttcctac acctagtgg              29

<210> SEQ ID NO 51
<211> LENGTH: 29
<212> TYPE: DNA
<213> ORGANISM: Artificial Sequence
<220> FEATURE:
<223> OTHER INFORMATION: Positive control

<400> SEQUENCE: 51 ggggggggggt tttttcccac tcctagtgg              29

<210> SEQ ID NO 52
<211> LENGTH: 29
<212> TYPE: DNA
<213> ORGANISM: Artificial Sequence
<220> FEATURE:
<223> OTHER INFORMATION: Positive control

<400> SEQUENCE: 52 ggggggggggt attttcctac tcctagtgg              29

<210> SEQ ID NO 53
<211> LENGTH: 29
<212> TYPE: DNA
<213> ORGANISM: Artificial Sequence
<220> FEATURE:

<223> OTHER INFORMATION: Positive control

<400> SEQUENCE: 53
gggggggggt attccccttc tcctagtgg                                29

<210> SEQ ID NO 54
<211> LENGTH: 29
<212> TYPE: DNA
<213> ORGANISM: Artificial Sequence
<220> FEATURE:
<223> OTHER INFORMATION: Positive control

<400> SEQUENCE: 54
gggggggggt actctgctac tcctagtgg                                29

<210> SEQ ID NO 55
<211> LENGTH: 29
<212> TYPE: DNA
<213> ORGANISM: Artificial Sequence
<220> FEATURE:
<223> OTHER INFORMATION: Positive control

<400> SEQUENCE: 55
gggggggggt atgttgctac acctagtgg                                29

<210> SEQ ID NO 56
<211> LENGTH: 29
<212> TYPE: DNA
<213> ORGANISM: Artificial Sequence
<220> FEATURE:
<223> OTHER INFORMATION: Positive control

<400> SEQUENCE: 56
gggggggggt atgttgctac gcctagtgg                                29

<210> SEQ ID NO 57
<211> LENGTH: 29
<212> TYPE: DNA
<213> ORGANISM: Artificial Sequence
<220> FEATURE:
<223> OTHER INFORMATION: Positive control

<400> SEQUENCE: 57
gggggggggt tttttccaac tcctagtgg                                29

<210> SEQ ID NO 58
<211> LENGTH: 29
<212> TYPE: DNA
<213> ORGANISM: Artificial Sequence
<220> FEATURE:
<223> OTHER INFORMATION: Positive control

<400> SEQUENCE: 58
gggggggggt attccccttc ccctagtgg                                29

<210> SEQ ID NO 59
<211> LENGTH: 29
<212> TYPE: DNA
<213> ORGANISM: Artificial Sequence
<220> FEATURE:
<223> OTHER INFORMATION: Positive control

<400> SEQUENCE: 59
gggggggggt atgttgctac tcctagtgg                                29

<210> SEQ ID NO 60
<211> LENGTH: 29
<212> TYPE: DNA
<213> ORGANISM: Artificial Sequence
<220> FEATURE:
<223> OTHER INFORMATION: Positive control

<400> SEQUENCE: 60
gggggggggt atgcccctc gcctagtgg                                29

<210> SEQ ID NO 61
<211> LENGTH: 29
<212> TYPE: DNA
<213> ORGANISM: Artificial Sequence
<220> FEATURE:
<223> OTHER INFORMATION: Positive control

<400> SEQUENCE: 61
gggggggggt atgttaacac ccctagtgg                               29

<210> SEQ ID NO 62
<211> LENGTH: 29
<212> TYPE: DNA
<213> ORGANISM: Artificial Sequence
<220> FEATURE:
<223> OTHER INFORMATION: Positive control

<400> SEQUENCE: 62
gggggggggt atgtacatac acctagtgg                               29

<210> SEQ ID NO 63
<211> LENGTH: 29
<212> TYPE: DNA
<213> ORGANISM: Artificial Sequence
<220> FEATURE:
<223> OTHER INFORMATION: Positive control

<400> SEQUENCE: 63
gggggggggt tttatcctac tcctagtgg                               29

<210> SEQ ID NO 64
<211> LENGTH: 29
<212> TYPE: DNA
<213> ORGANISM: Artificial Sequence
<220> FEATURE:
<223> OTHER INFORMATION: Positive control

<400> SEQUENCE: 64
gggggggggt attatcctac ccctagtgg                               29

<210> SEQ ID NO 65
<211> LENGTH: 29
<212> TYPE: DNA
<213> ORGANISM: Artificial Sequence
<220> FEATURE:
<223> OTHER INFORMATION: Positive control

<400> SEQUENCE: 65
gggggggggt attcccttc ccctagtgg                                29

METHOD OF DESIGNING DNA PROBE CHIP FOR ROOM TEMPERATURE HYBRIDIZATION AND THE DNA PROBE CHIP

CROSS REFERENCE TO RELATED APPLICATIONS

The present application is based on, and claims priority from, Korean Patent Application No. 2007-0117736, filed Nov. 19, 2007, and Korean Patent Application No. 2008-0093800, filed Sep. 24, 2008, the disclosure of which is hereby incorporated by reference herein in its entirety.

BRIEF DESCRIPTION OF DRAWINGS

FIG. 8 is a diagram showing DNA probe whose sequence starts at the position between −8 and +3, when setting the 3'-terminal of the primer as 0.

Each DNA probe was designed to have consecutive guanine bases such that they can be immobilized on the chip prepared according to FIG. 1 and FIG. 2. FIG. 8 is a diagram showing that the thus-prepared DNA chip carries out room-temperature hybridization with a PCR product with high specificity and sensitivity.

FIG. 10 illustrates the results of actual experiments and shows that in the hybridization experiment using directly template DNA not treated PCR process, when the +15 mer used, the fluorescence intensity is not observed even if reaction solution is spreaded in which concentration of template DNA is 60 ng/μl, when the 0 mer and 8 mer used, the fluorescence intensity is enough to analyze within reaction solution in which concentration of template DNA is 20 ng/μl and the efficiency of hybridization is dramatically increased observed.

TECHNICAL FIELD

Figures 1, 1A:
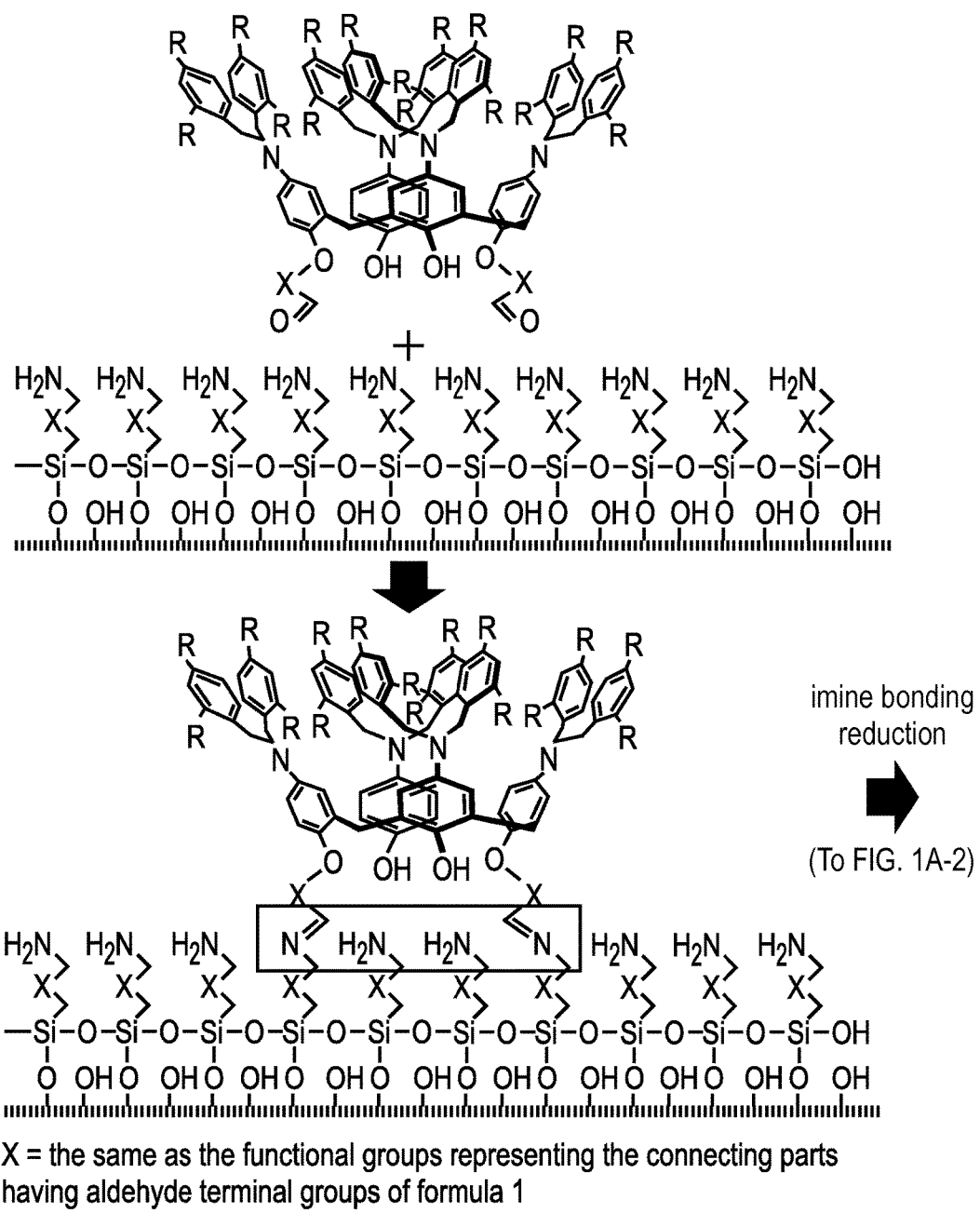
FIG. 1A and FIG. 1B are diagrams showing the process of preparing a glass slide spread with a monolayer of an aminocalixarene derivative or a monolayer of an iminecalixarene derivative, which recognizes consecutive guanine bases.

Since Affymetrix Co. of U.S.A disclosed the technology of preparing a DNA chip by using the surface photosynthesis technology using a photomask, various technology for preparing a DNA chip have been developed. Among them, the conventional method of preparing a DNA chip by bonding a probe having an amine functional group on an aldehyde chip, and the method of preparing a DNA chip by simultaneously immobilizing oligo-DNAs having consecutive guanine bases of Biometrix Technology Inc. to form a monolayer are disclosed. Presently, various DNA chips including a DNA chip for genotyping HPV, a DNA chip for genotyping tuberculosis virus, and the like are being developed worldwide.

One of the biggest problems restricting the use of such DNA chips is due to high-temperature hybridization. Generally, DNA hybridization on a DNA chip are carried out at a high temperature of about 40° C.~50° C. The major reason for carrying out the hybridization at such a temperature is because, on a DNA chip, ten to several hundred probes designed to be selectively hybridized with different types of DNAs are immobilized on a small space of the same size, and thus because the hybridzation has to be carried out at a high temperature in order to increase the specificity and minimize non-specific reaction when each probe is hybridzed with a PCR product or a template DNA.

Most of the currently used DNA chips are prepared by designing and immobilizing a probe which can be hybridized at such high temperatures. On said DNA chip, a solution containing DNAs is spreaded, and then the chip is heated to a high temperature of 40° C.~50° C. or higher, and then hybridization is carried out for about 30 minutes to 2 hours. In this regard, the amount of DNAs bonded to the probe immobilized on a DNA chip changes depending on the concentration of the DNAs in the solution rather than on the total mount of the DNAs. Accordingly, it is common to use as small as possible amount of a solvent when spreading DNAs. However, in such case, there are cases that the spreaded solution dries during the process of maintaining the temperature high. Thus, a proper amount of solvent is used when using a DNA chip utilizing high-temperature hybridization. In addition, in the case of a DNA chip utilizing high-temperature hybridization, the immobilized probe to be hybridized is designed to be optimally bonded to DNA at a predetermined temperature. Accordingly, if the temperature is too high, the amount of the bonded DNAs decreases, and if the temperature is too low, probes which should not be bonded are also bonded to the DNAs, which hinders precise genotyping. Notwithstanding the above problems, in conventional technology of designing a probe and conventional methods used for the hybridization for genotyping, such as a DNA chip, the temperature should be raised to a high temperature, since the specificity for genotypes can be improved at a high temperature rather than at a room temperature.

In order to solve such problems, the present inventors developed novel technology of designing a probe which can achieve high speicificity even in the case of carrying out hybridization at a room temperature (20° C.~30° C.), and which can be bonded to DNA with high sensitivity; that is, which can be bonded to many DNAs. It was confirmed that, on a DNA chip prepared by immobilizing the thus designed probe, DNAs were selectively bonded to the probe on the chip by hybridization while maintaining maximum specificity for each genotype and achieving higher sensitivity than that of high-temperature hybridization. At the same time, it was confirmed that the hybridization proceeded minimizing the non-specificity of bonding. By using such probe design technology, a probe used for genotyping HPV which can carry out hybridization at a room temperature (20° C.~30° C.) is designed. In addition, a DNA chip for genotyping HPV where the thus designed probes are immobilized was prepared. Then, DNAs such as PCR products were spreaded, and the sensitivity and specificity for genotypes were measured. From the results, it was confirmed that the newly designed probes are hybridized at a room temperature and DNAs are bonded to the probes with high specificity and higher sensitivity than that of high-temperature hybridization, thus making possible an efficient genotyping. The results relating to the above achievement are described in the present application.

DETAILED DESCRIPTION

The objective of the present invention is to develop new technology of designing a probe capable of genotyping by carrying out room-temperature (20° C.~30° C.) hybridization to solve the problems occurring when using conventional DNA chips for genotyping carrying out high-temperature hybridization. The present invention also developed a DNA chip capable of carrying out room-temperature hybridization and genotyping, prepared by immobilizing probe DNA oligomer designed according to the method of the present invention. The DNA chip was prepared by immobilizing oligomer probes having more than 7 guanine bases, preferably 7~15 guanine bases, on the DNA chip prepared according to the method of FIG. 1 and FIG. 2.

Figure 5A:
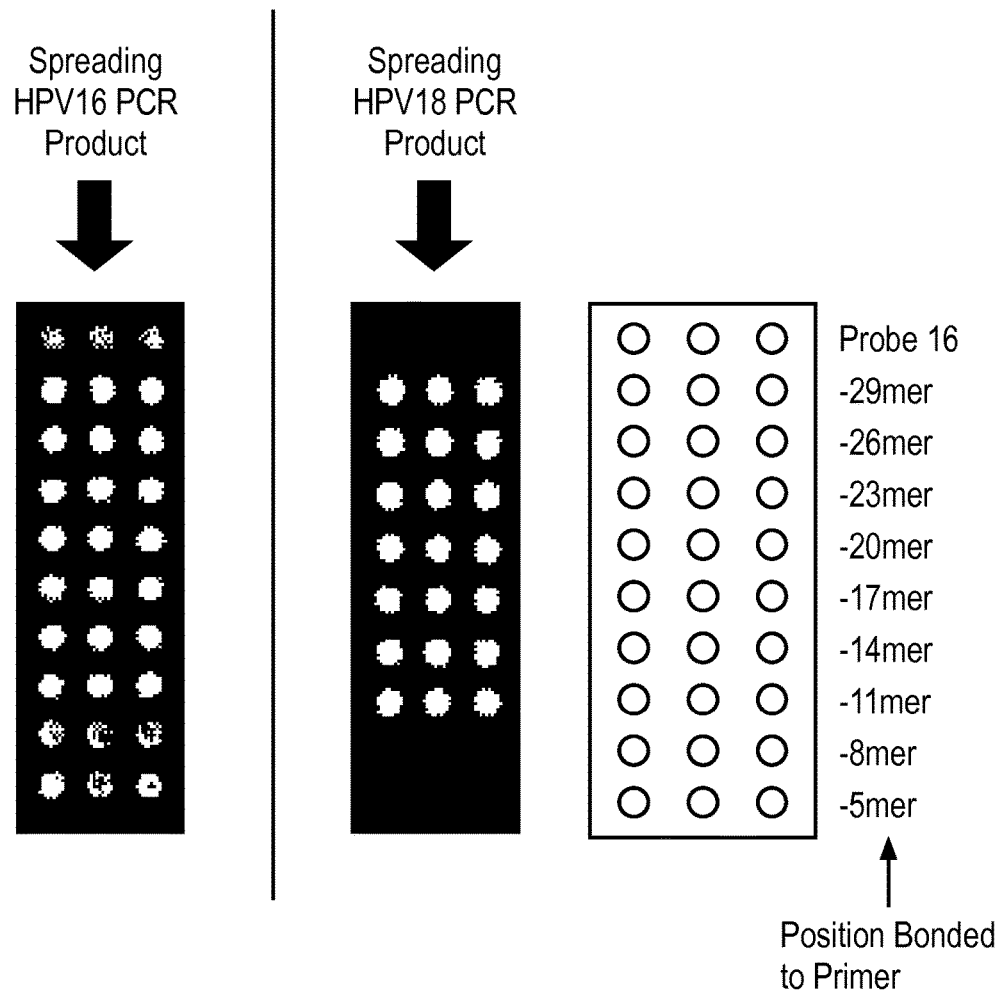
FIG. 5 illustrates the results of actual experiments and shows the method of determining positive control and the thus determined positive control. For the PCR product of each genotype, the sequence of positive control standard probe was designed between the twelfth base position which is 12 bases far from the first base at the end of the 3'-terminal of primer and – position which is indicated the number of overlapped bases with the primer (in the case where the base sequence has five overlapping bases, it was described with −5; in the case where the base sequence has eight overlapping bases, it was described with −8; and if the base sequence has eleven overlapping bases, it was described with −11). Then, the PCR product of a HPV standard template was spreaded onto a DNA chip where such a standard probe is immobilized. From the results, it was confirmed that the probe (−5) designed such that 5 mer overlaps with a primer and the probe (−8) designed such that 8 mer overlaps with a primer did not exhibit signals if they are not complementary to the spreaded genotypes, whereas the standard probe (positive control, −11) designed such that 11 mer overlaps with a primer is bonded with all types of PCR products or primers to show fluorescence. Therefore, a positive control was designed to start −5~−8 position.
Figure 5B:
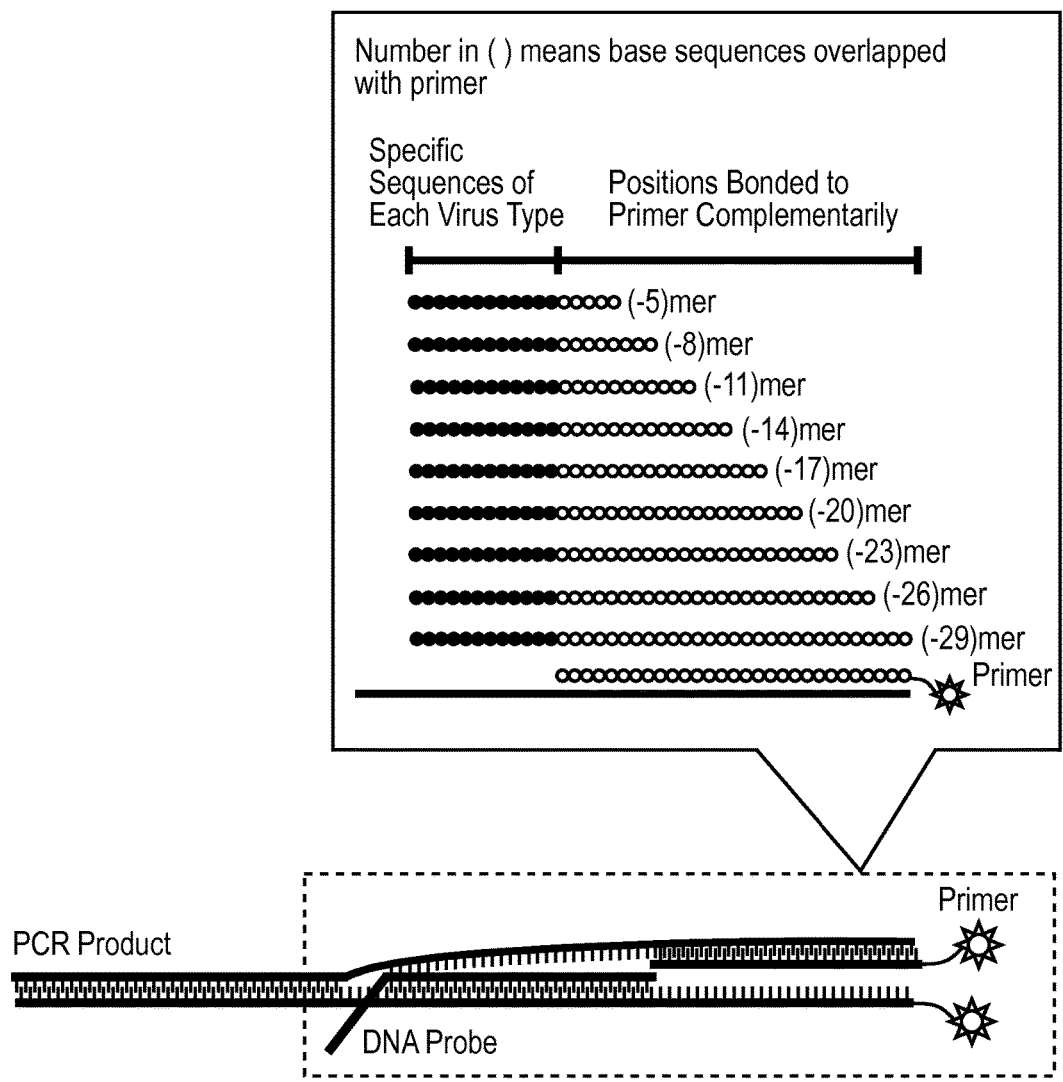
Figures 1, 6A:
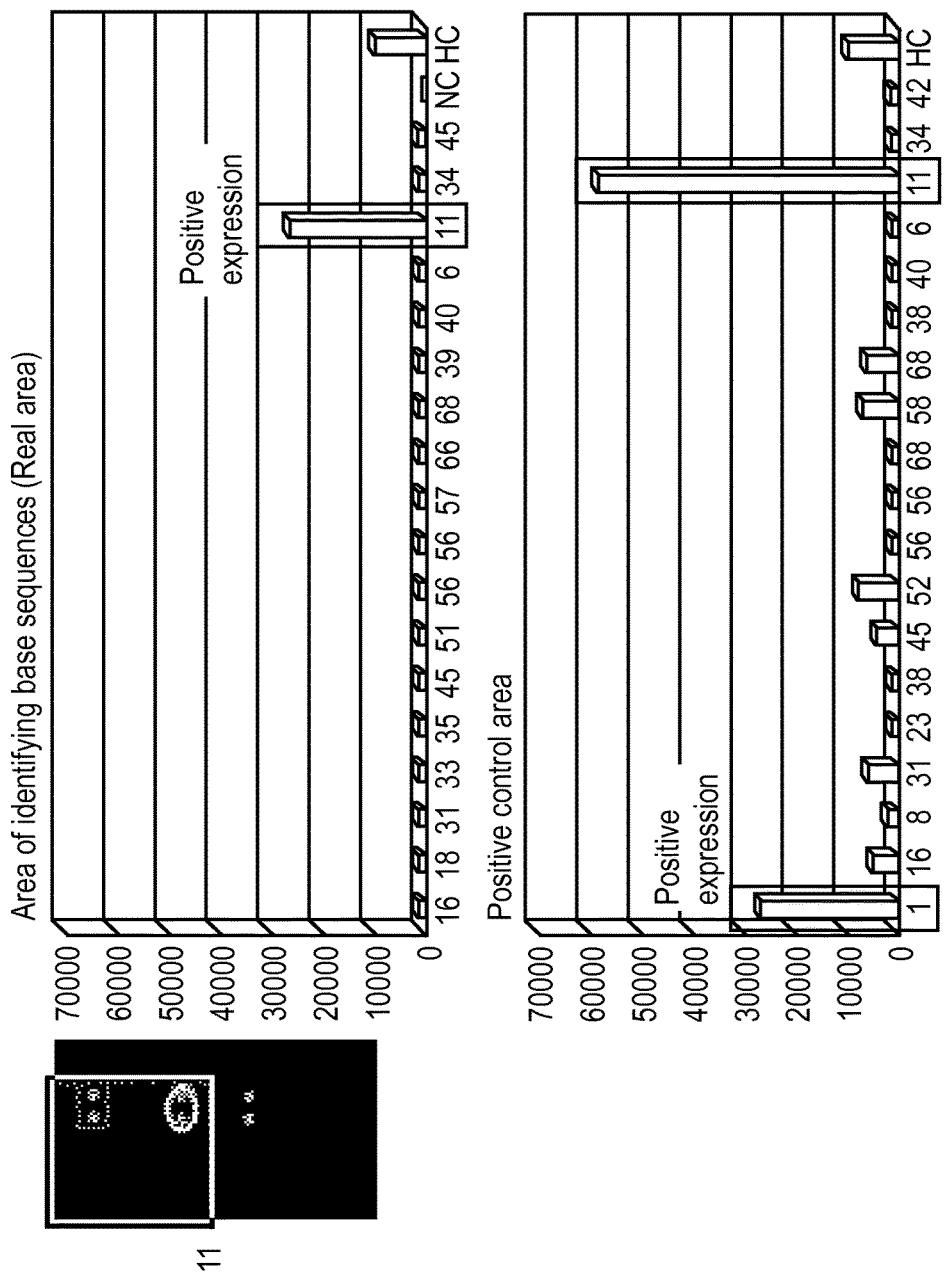
FIG. 6A and FIG. 6B show the process of designing and determining a standard probe, i.e, positive control, to provide a standard for differentiating the signals obtained by specific bonds and non-specific bonds and thereby to carry out precise genotyping. It shows the result of actual experiments carried out after spreading the PCR product which amplified with template DNA of each genotype on a real area where the probes of the genotypes according to Table 4 are immobilized and on the area of a positive control on a DNA chip where 20 mer probes candidate (Table 6) obtained by combining the −8 mer base sequence determined in FIG. 5 with the 12 mer probes for each genotype of Table 4 at the 3'end of the probes are immobilized. The results are summarized in Table 7. Then, PCR products of specific HPV types were immobilized, and then 6 probes showing signals for many types of PCR products were selected as candidates for standard probes. Then, mixed standard probes for a positive control on a DNA chip were made by mixing said probes as in Table 8 and immobilizing them.
Figures 1, 6A:
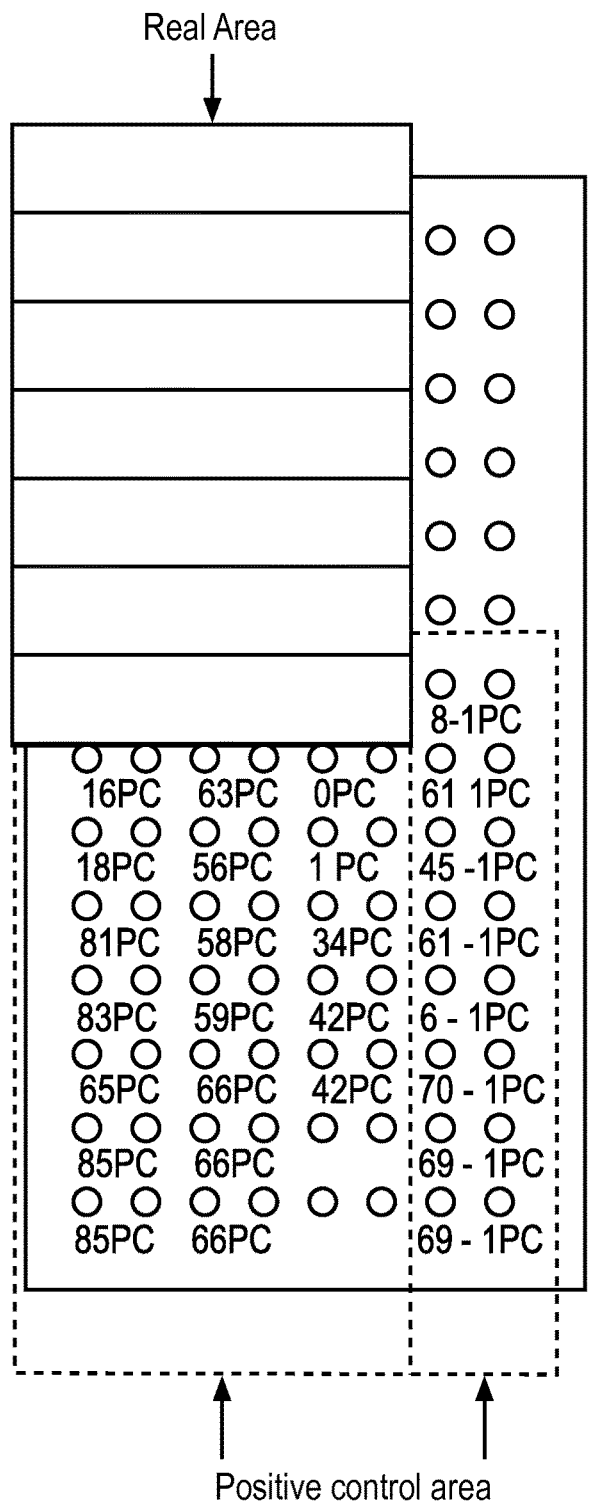
Figures 2, 6A:
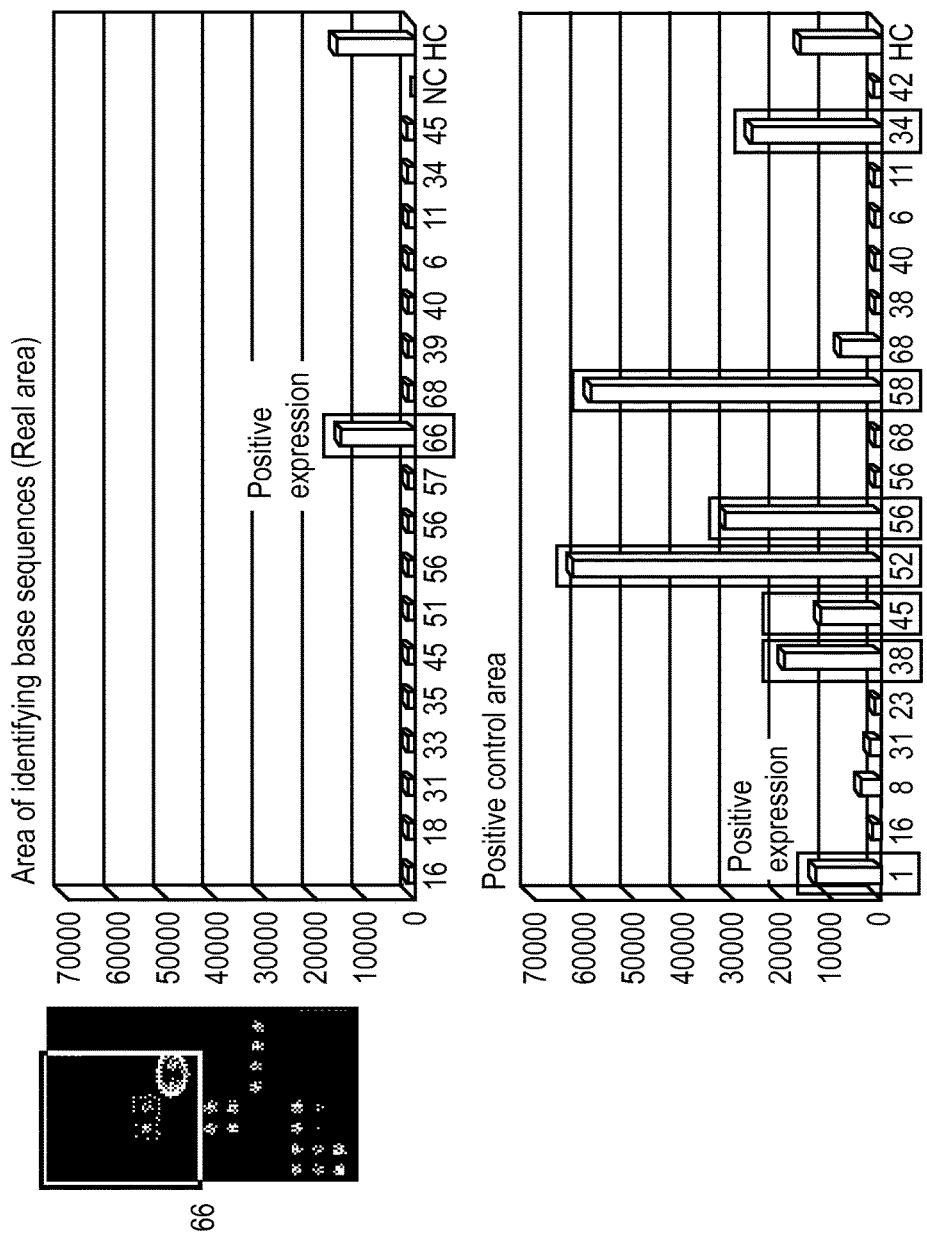
Figures 2, 6A:
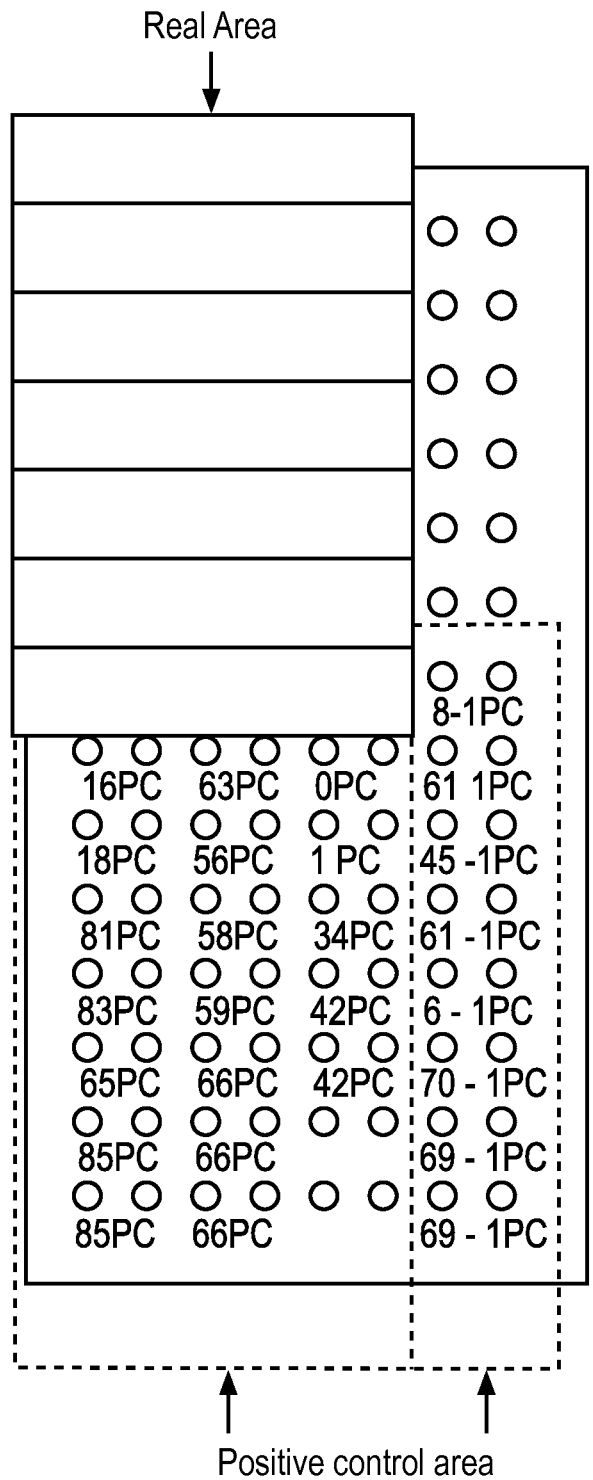
Figure 6B:
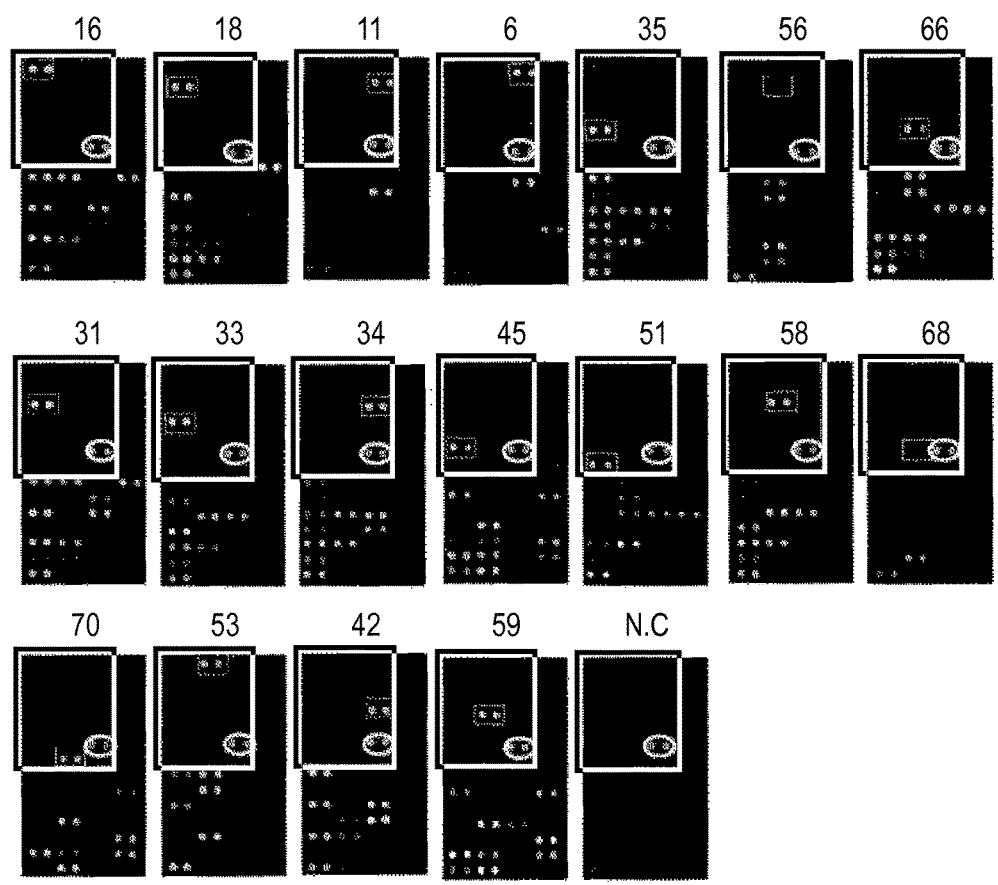
Figure 6B:
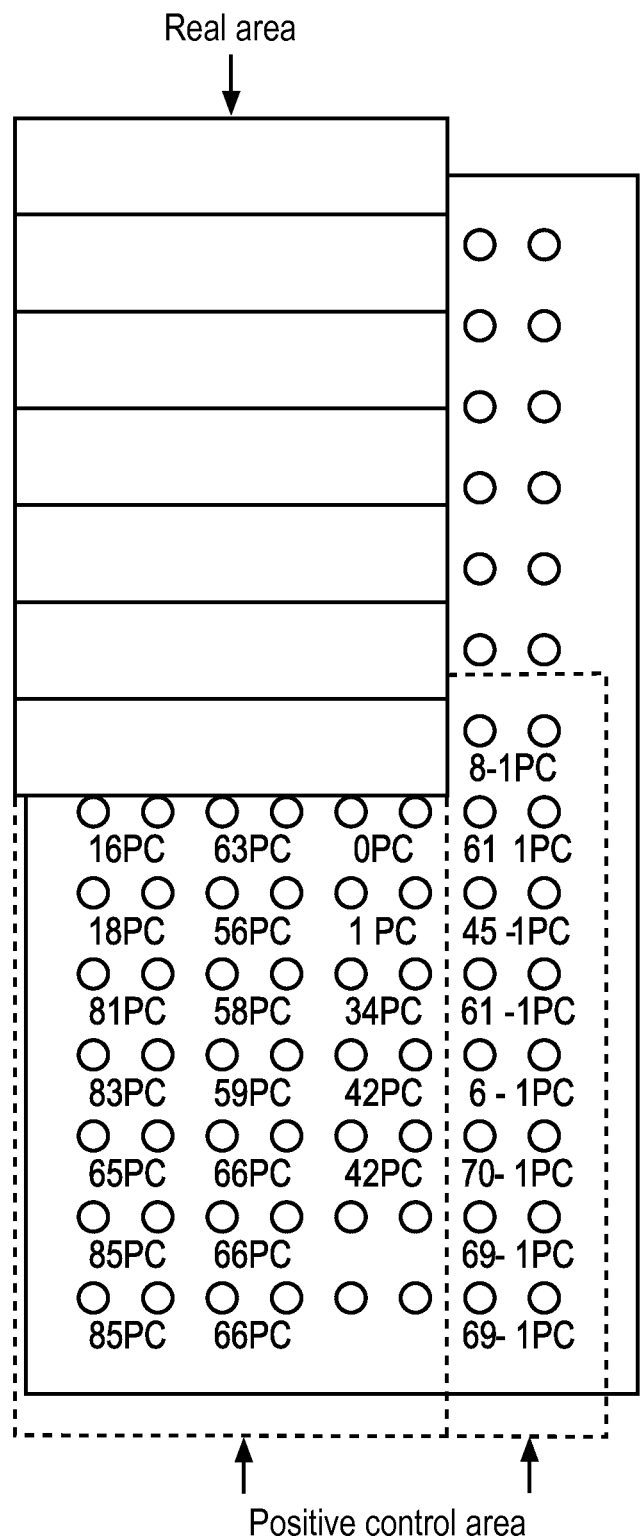
Figures 1, 7A:
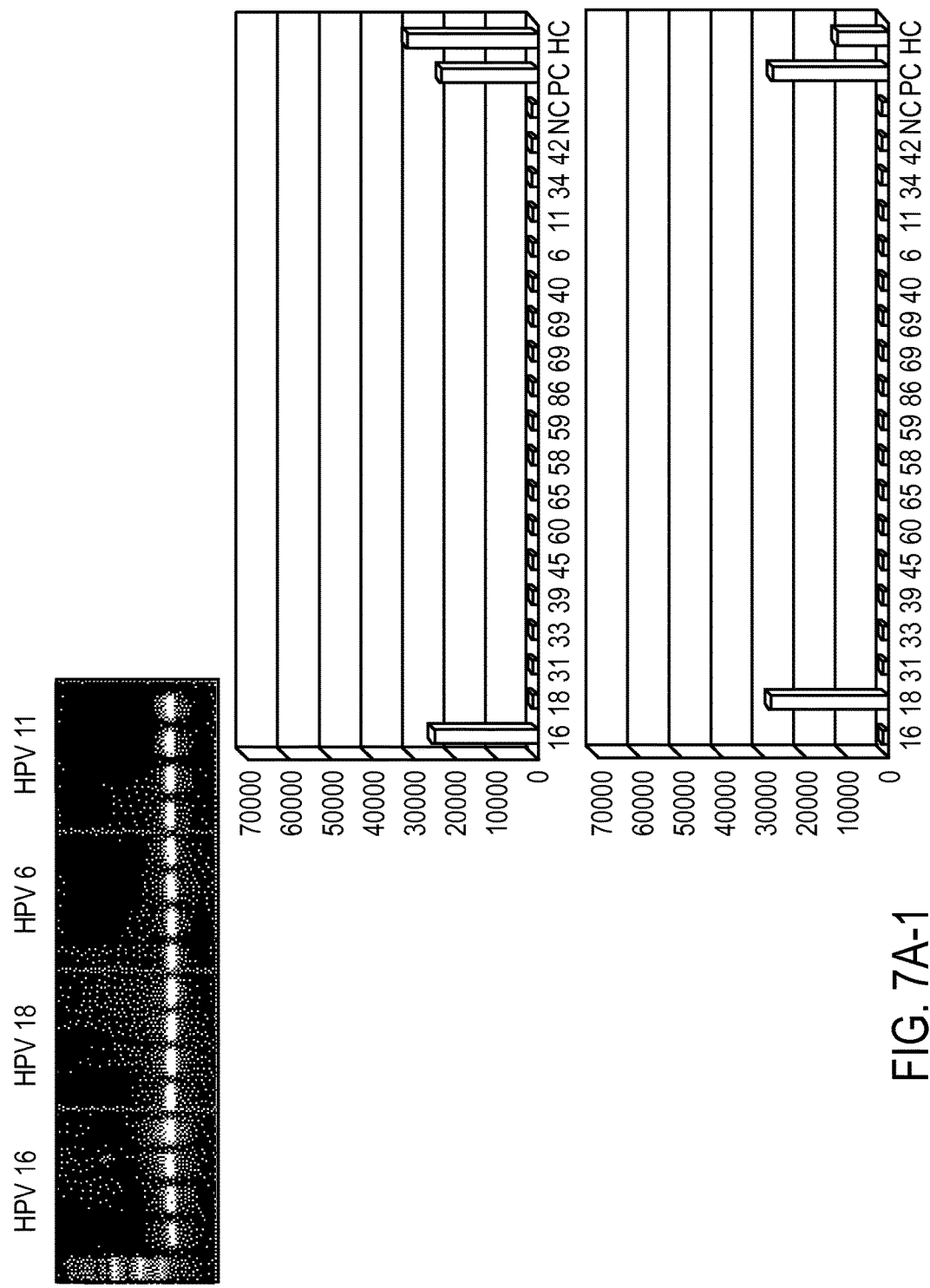
FIG. 7A, FIG. 7B, FIG. 7C, FIG. 7D and FIG. 7E show the results of repeated experiments obtained by spreading the products obtained by PCR amplifying standard templates of each type using the primer set of Table 2 on a DNA chip for room-temperature hybridization prepared by immobilizing the two mixed types of positive controls determined in FIG. 6A and FIG. 6B, the negative control (position to measure the nonspecificity) of Table 8, a hybridization control (a position where a fluorescence-labled primer is attached, which identifies whether a consistent amount of PCR product was input) and the DNA probes of 18 HPV types of Table 4. The results show that when using a DNA chip capable of carrying out room-temperature hybridization, fluorescence of each HPV types is observed exactly at a positive control and at positions of the probes of each type, and the amount of spreaded PCR products can be calculated by using the fluorescence intensity of the position of a hybridization control, and that nonspecific bonds are almost removed as compared to a DNA chip carrying out high-temperature hybridization.
Figure 7A:
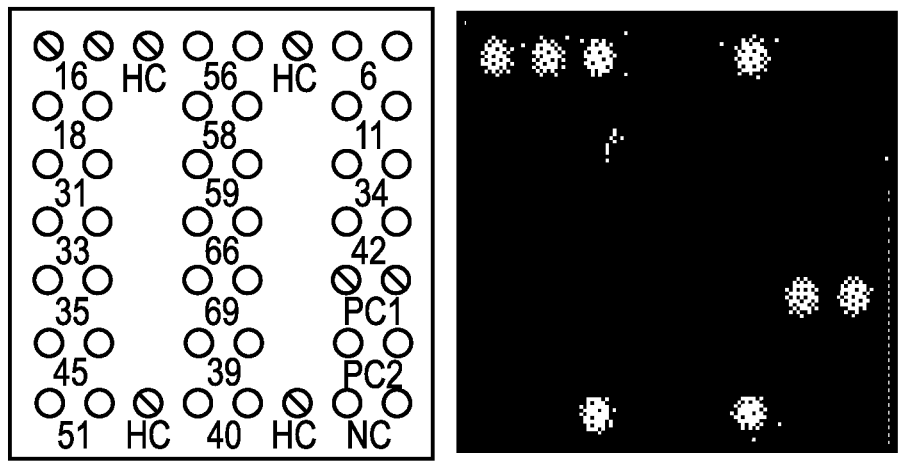
Figure 1:
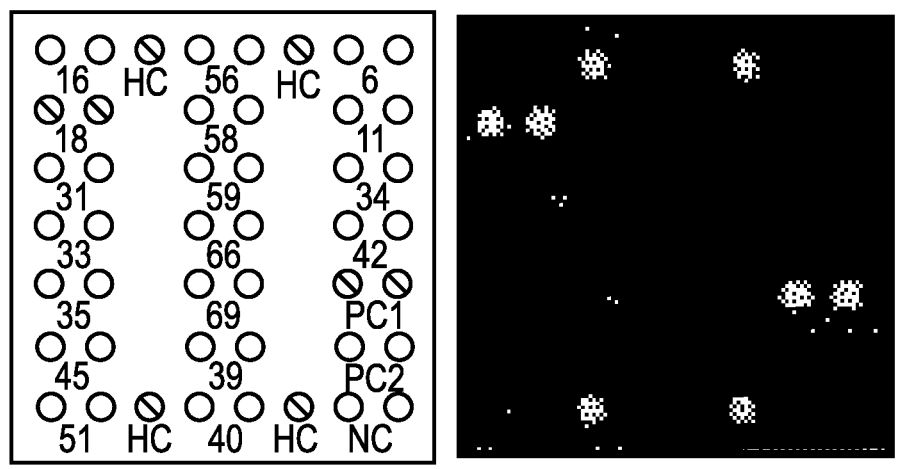
Figures 2, 7A:
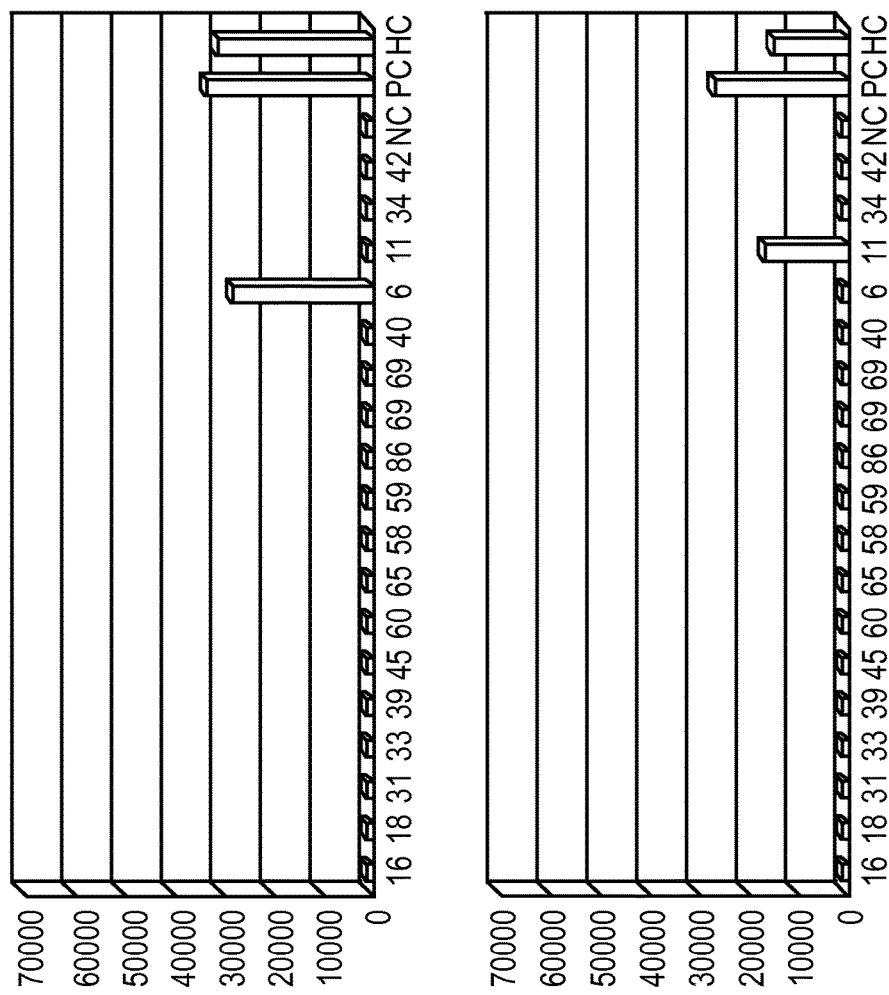
Figure 7A:
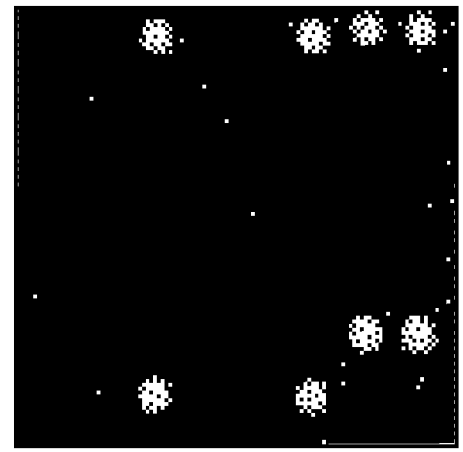
Figure 2:
Figures 1, 7B:
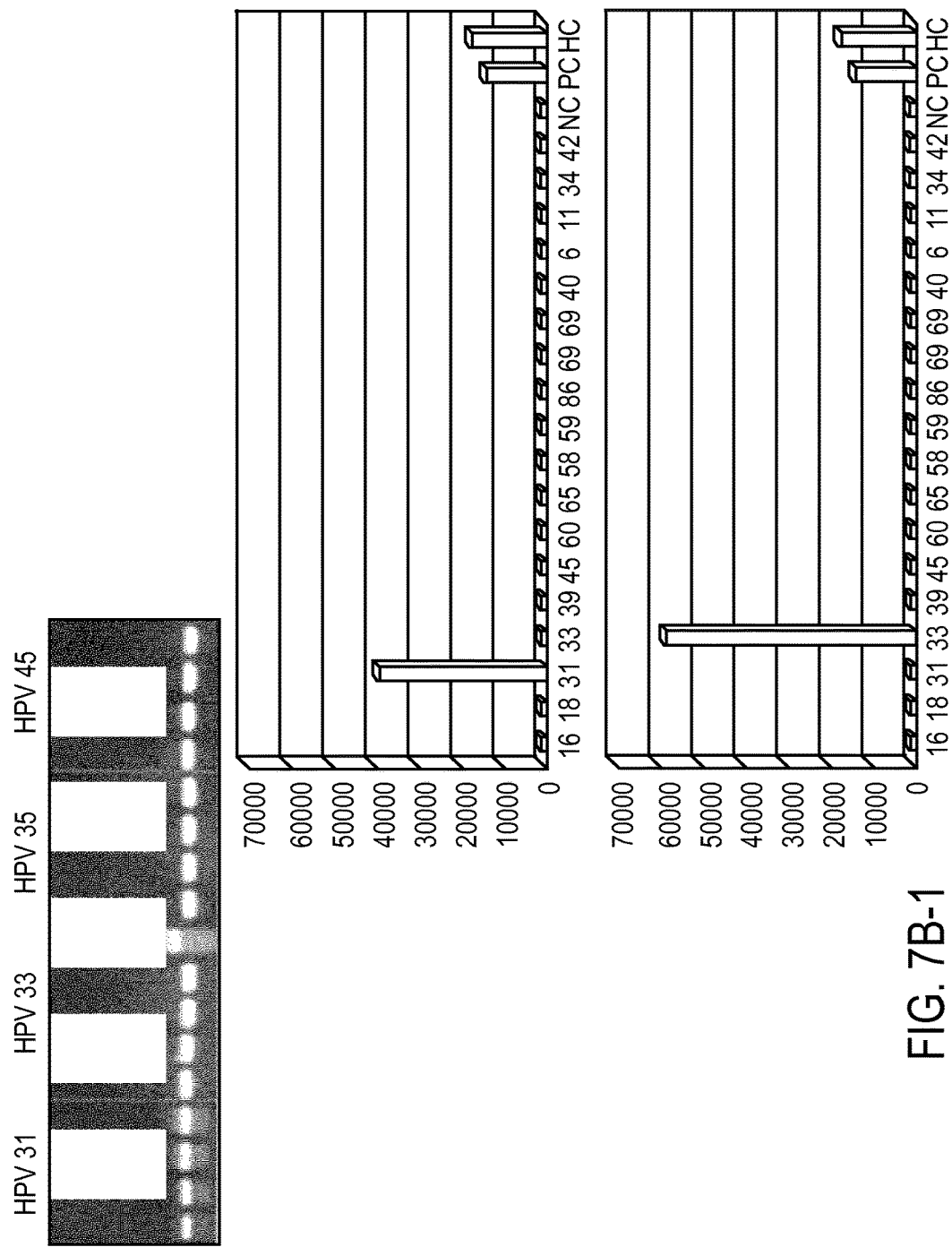
Figure 7B:
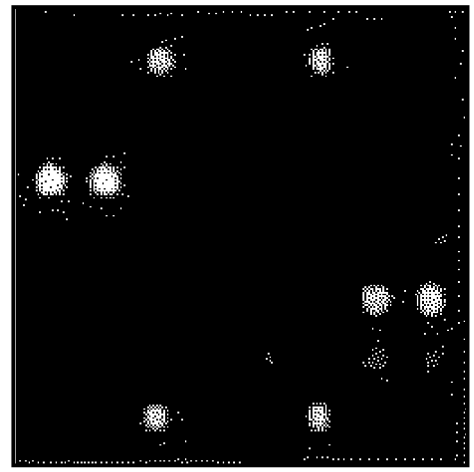
Figure 1:
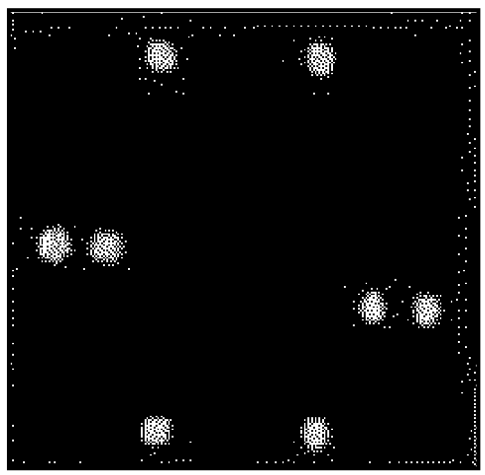
Figure 7B:
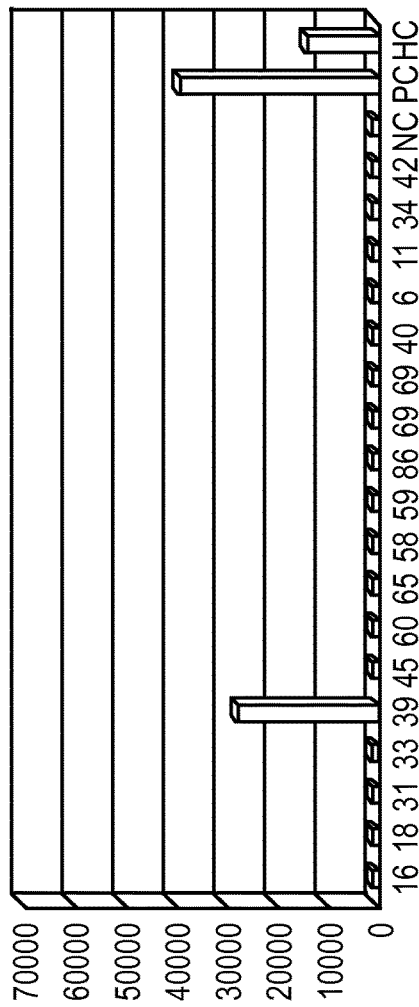
Figure 2:
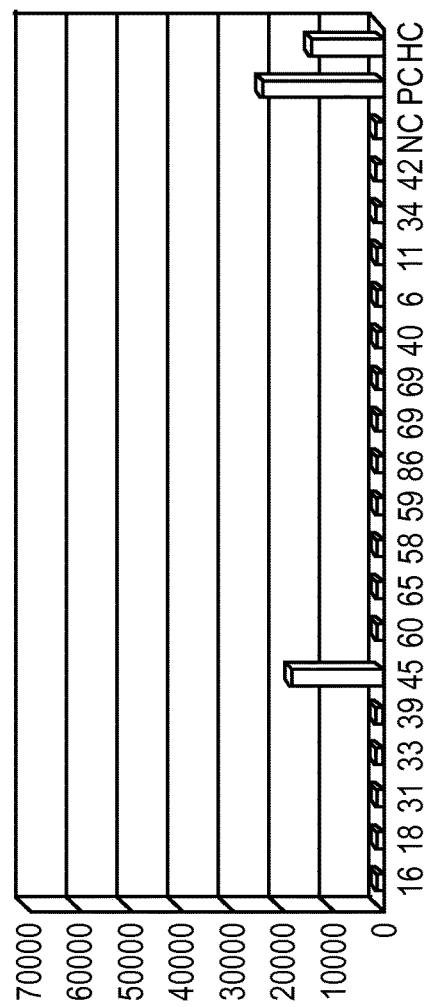
Figure 7B:
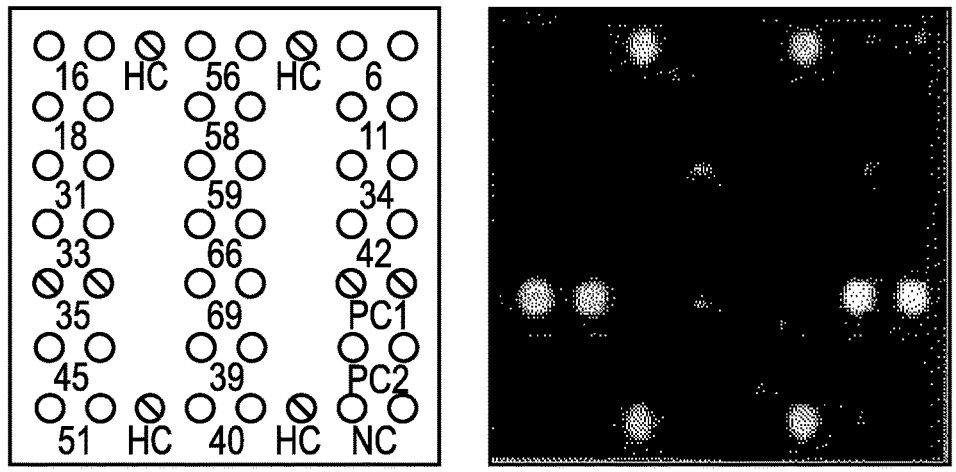
Figure 2:
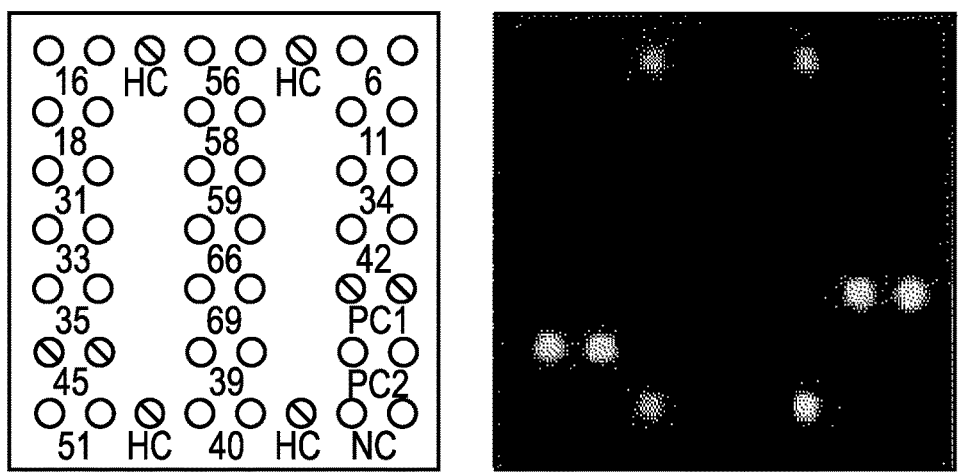
Figures 1, 7C:
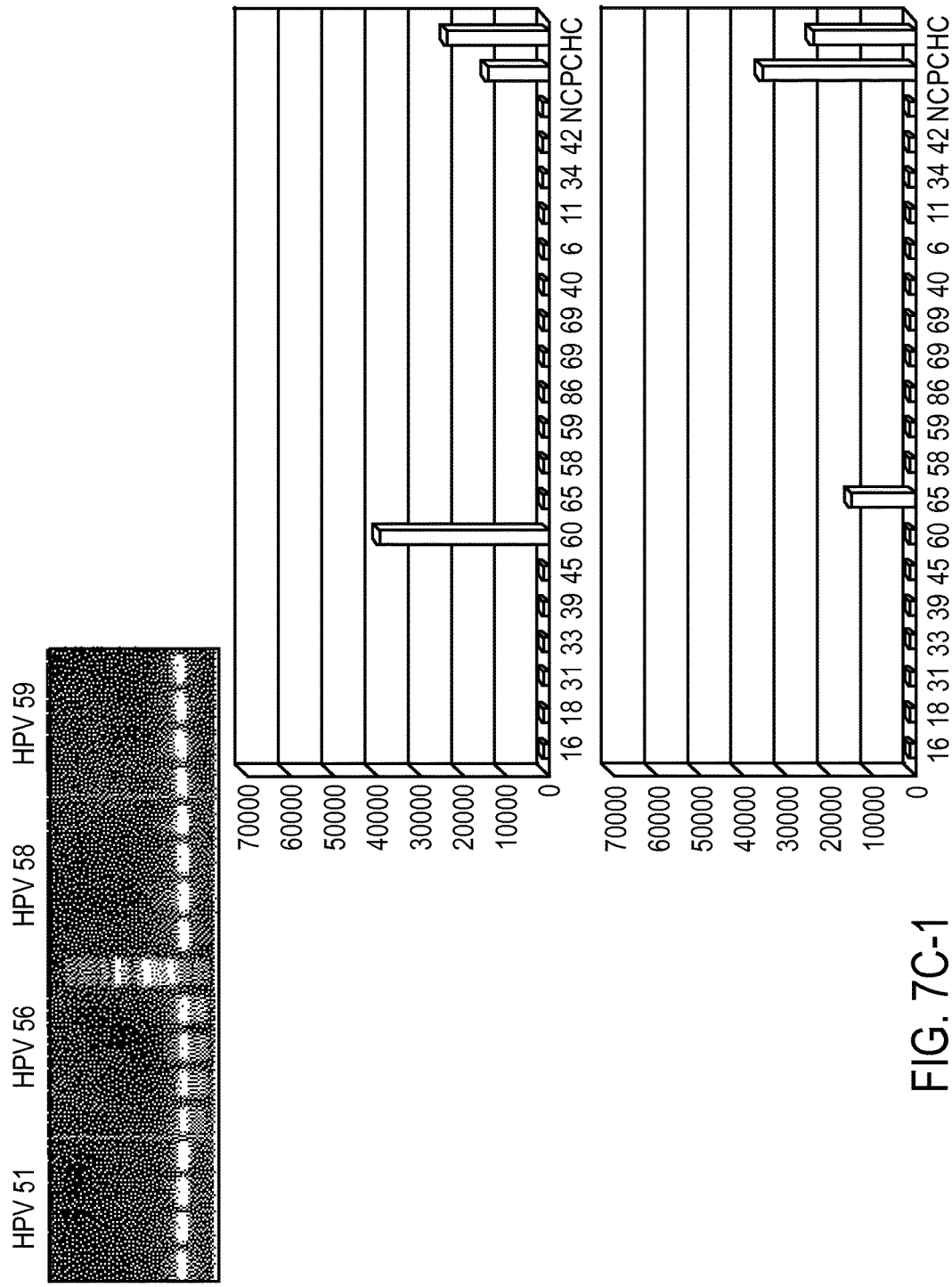
Figures 2, 7C:
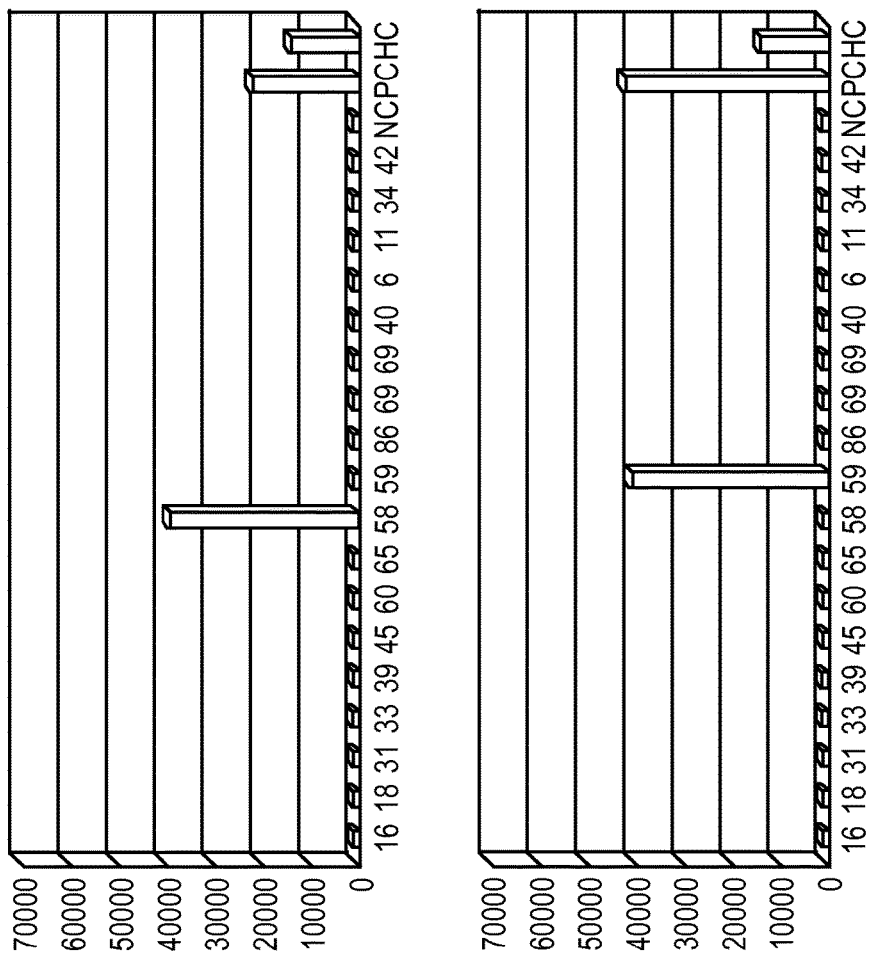
Figure 7C:
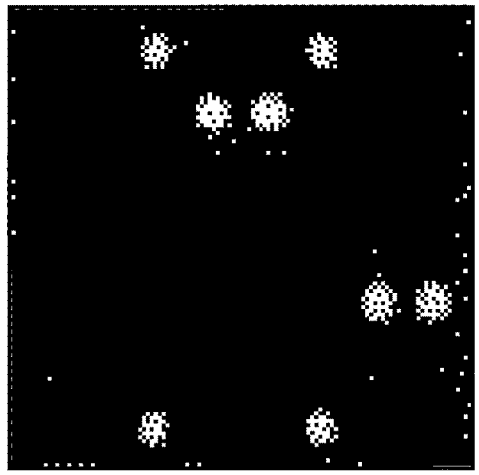
Figure 2:
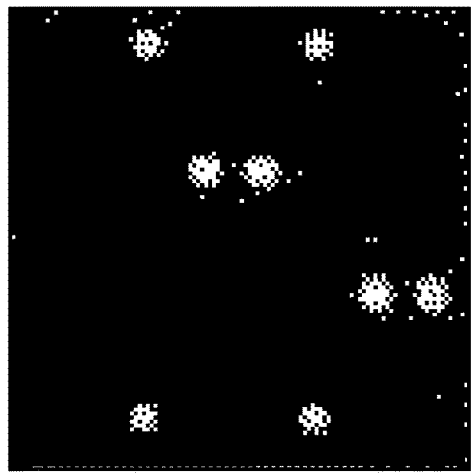
Figures 1, 7D:
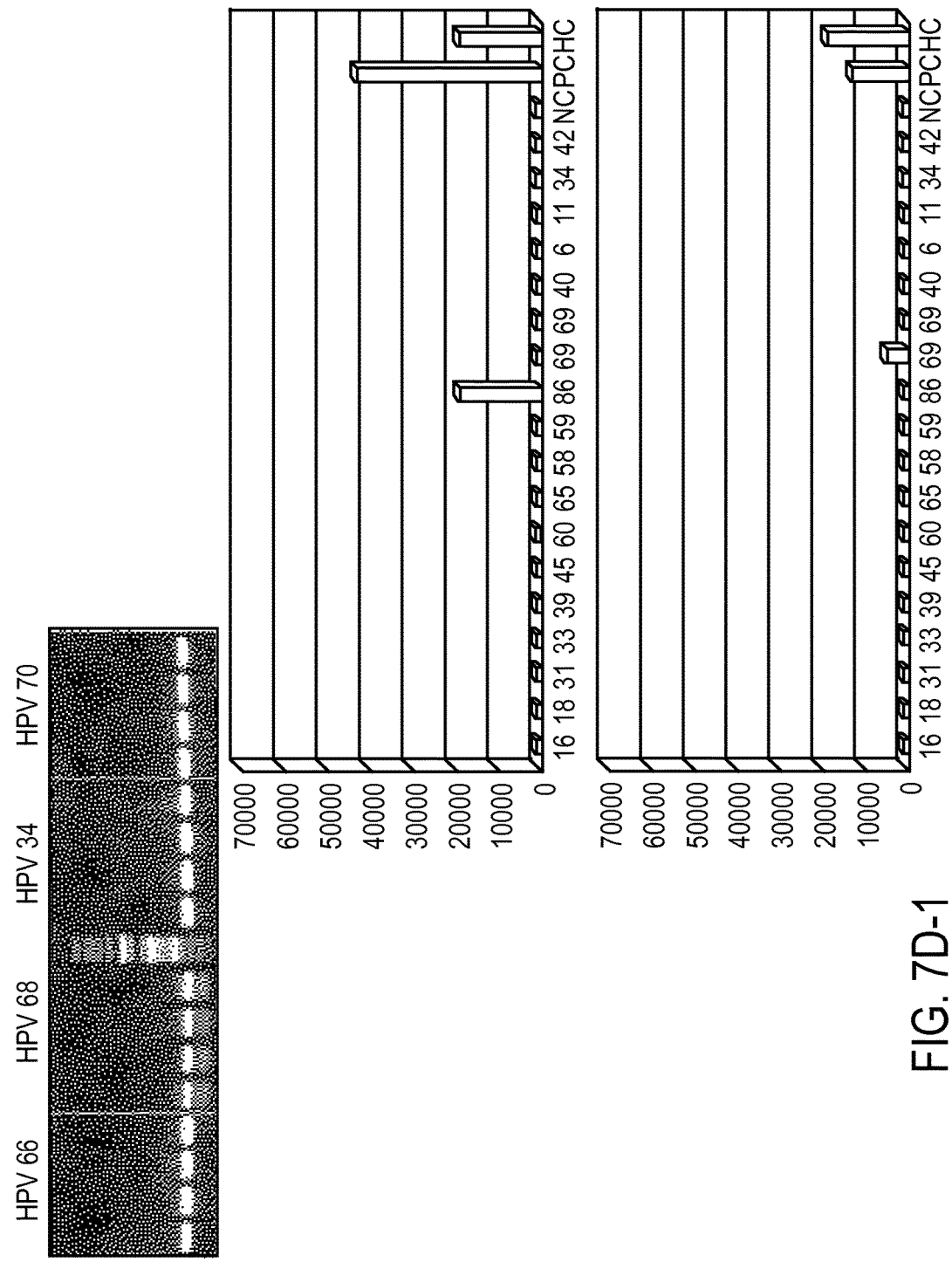
Figure 7D:
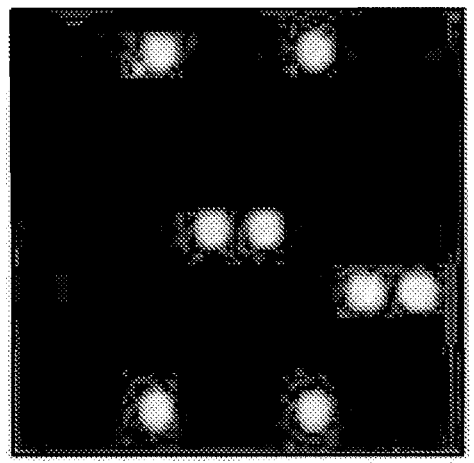
Figure 1:
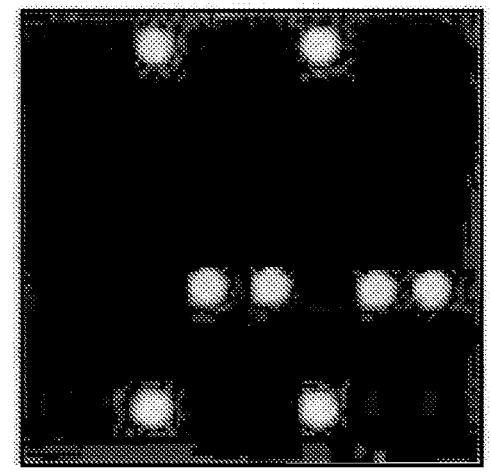
Figures 2, 7D:
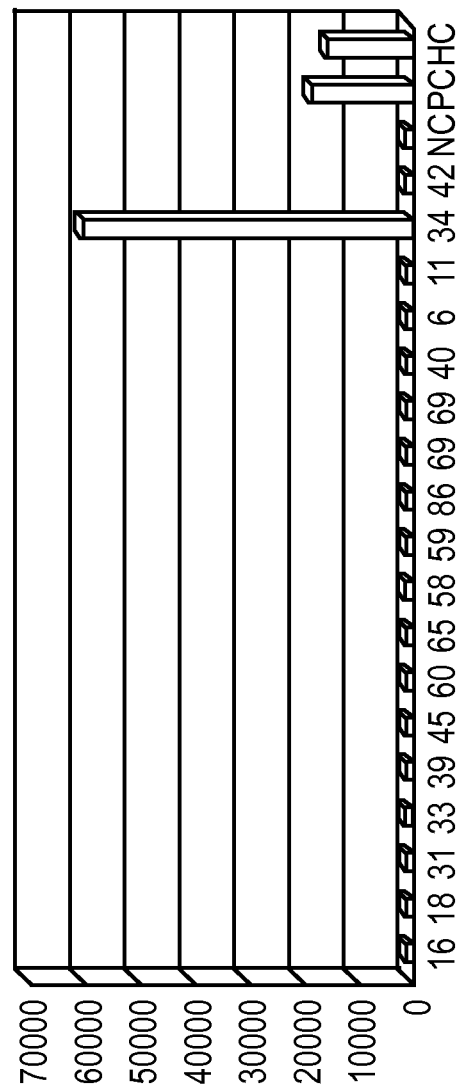
Figures 2, 7D:
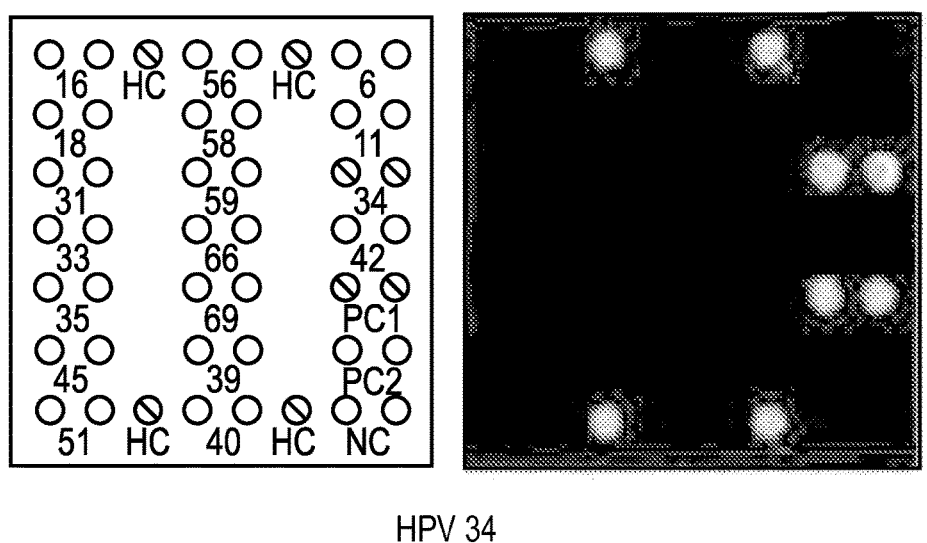
Figure 7E:
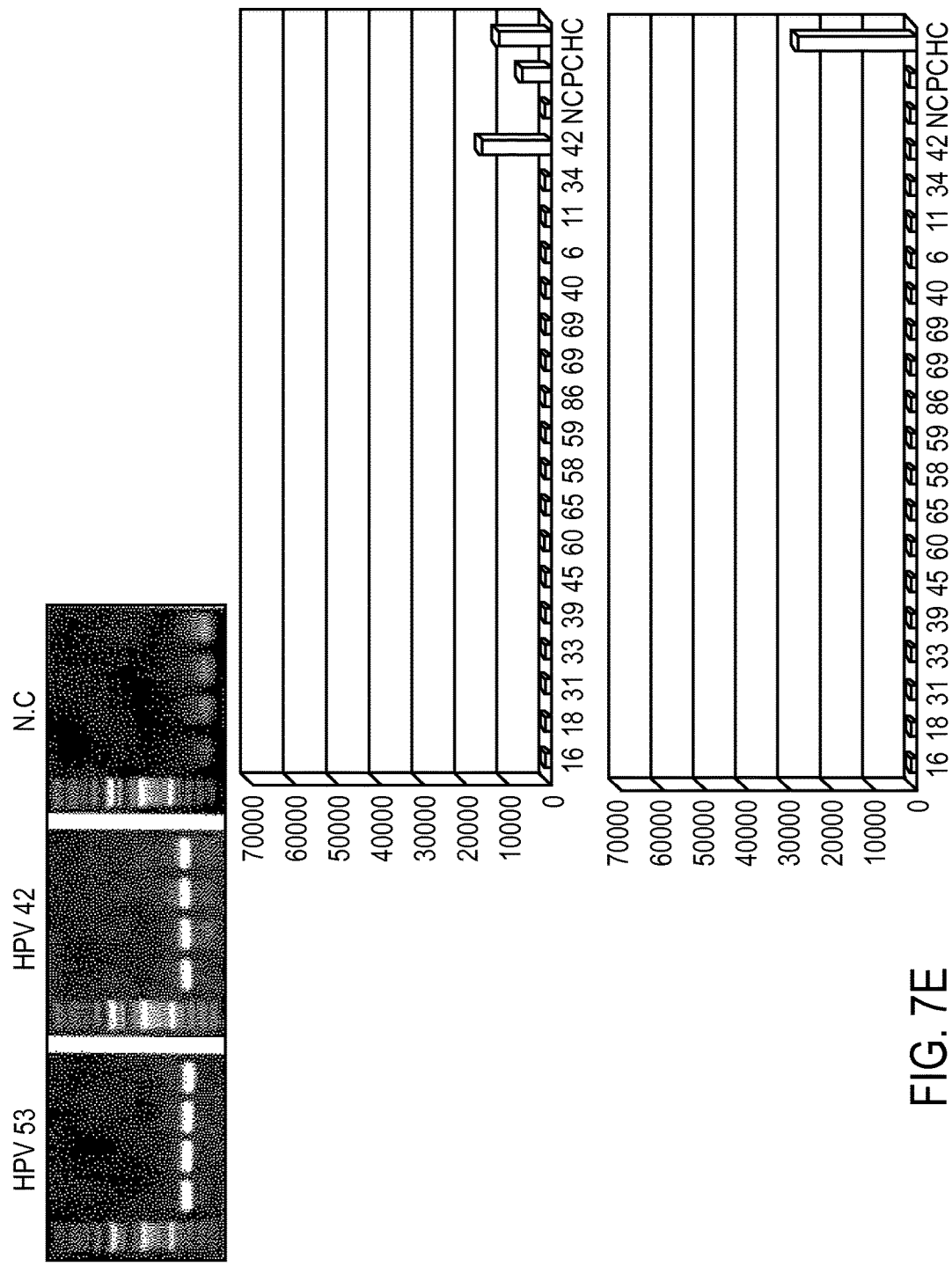
Figure 7E:
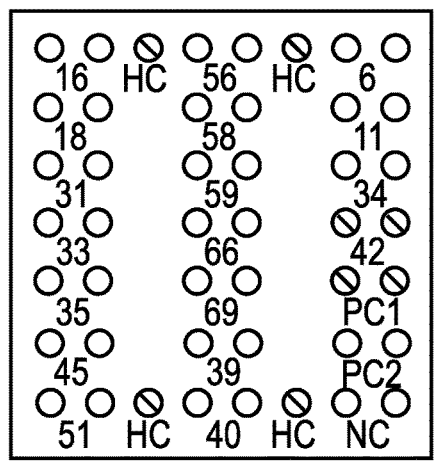
Figure 7E:
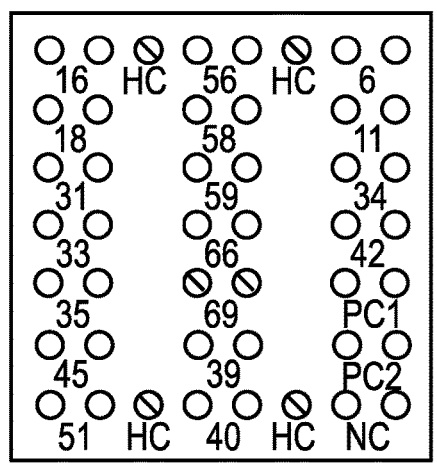

The DNA chip for carrying out room-temperature hybridization according to the present invention and a DNA chip for carrying out high-temperature hybridization of were compared for sensitivity and specificity by using actual PCR products. By using the comparison results, the technology of designing a probe which can exhibit stronger signals when carrying out room-temperature hybridization and the new technology of designing a probe which can remove nonspecific bonding as many as possible were developed. In addition, such technology was applied to a probe design. FIG. 3 shows the results that when a room-temperature hybridization is carried out on a DNA chip where the probes prepared according to the method of FIG. 8 and FIG. 9 based on the results of FIGS. 3, 4 and 5 are immobilized, errors due to nonspecific fluorescence expressing, i.e. nonspecific bonding are minimized (here, nonspecific bonding refers to a bonding made at a position where fluorescence should not be visible, and thereby misleading people to believe that a corresponding genotype is present).

Figure 8:
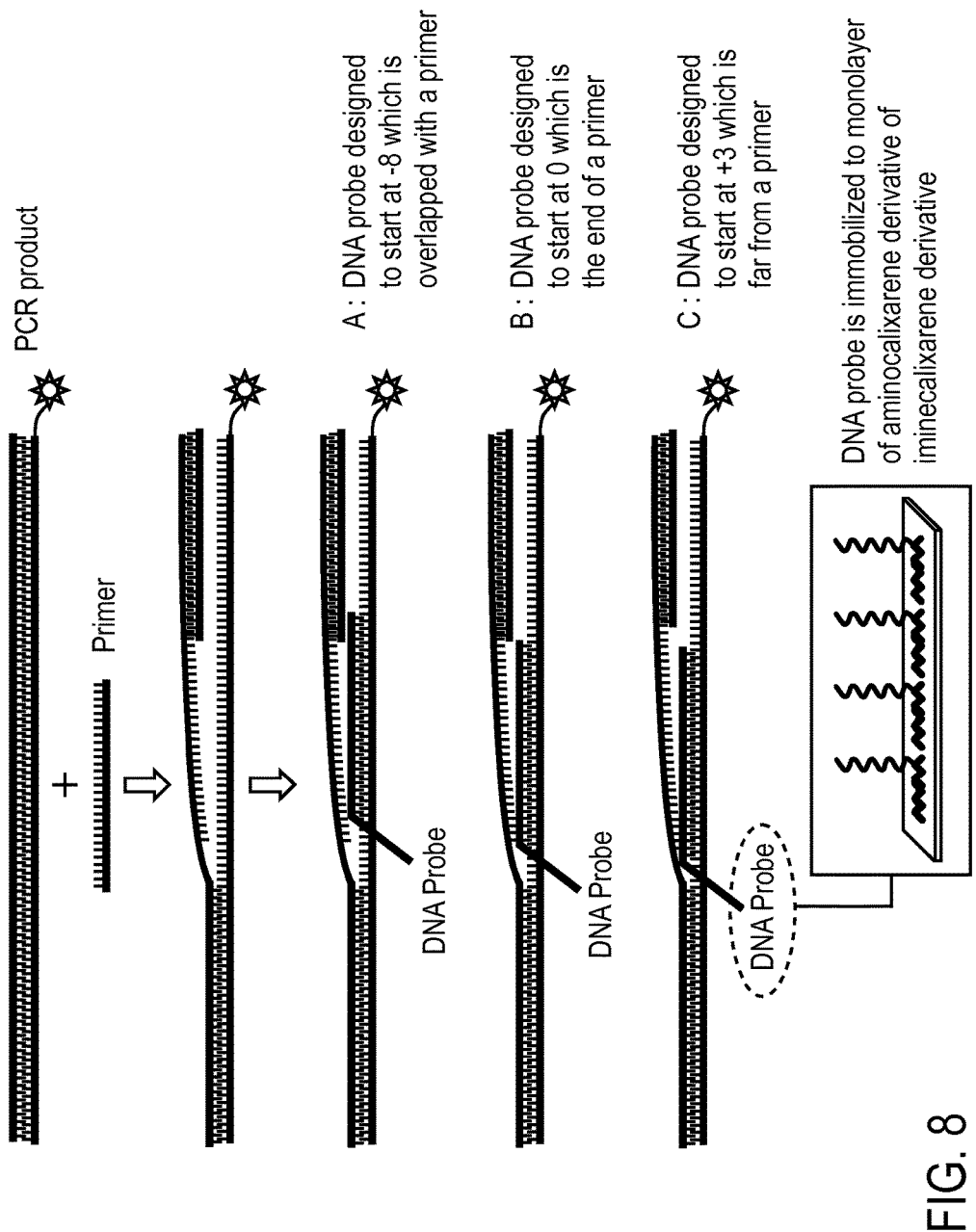
FIG. 8 is a diagram of a probe designed to have 8 sequence overlapped with the primer which is used for PCR and hybridzed with a PCR product (e.g., designed to start at −8), and a probe designed to start at the end of the primer, i.e. 0 sequence far from the primer (e.g., designed to start at 0), and a probe designed to start at 3 sequence far from the primer (e.g., designed to start at +3). That is.
Figure 9:
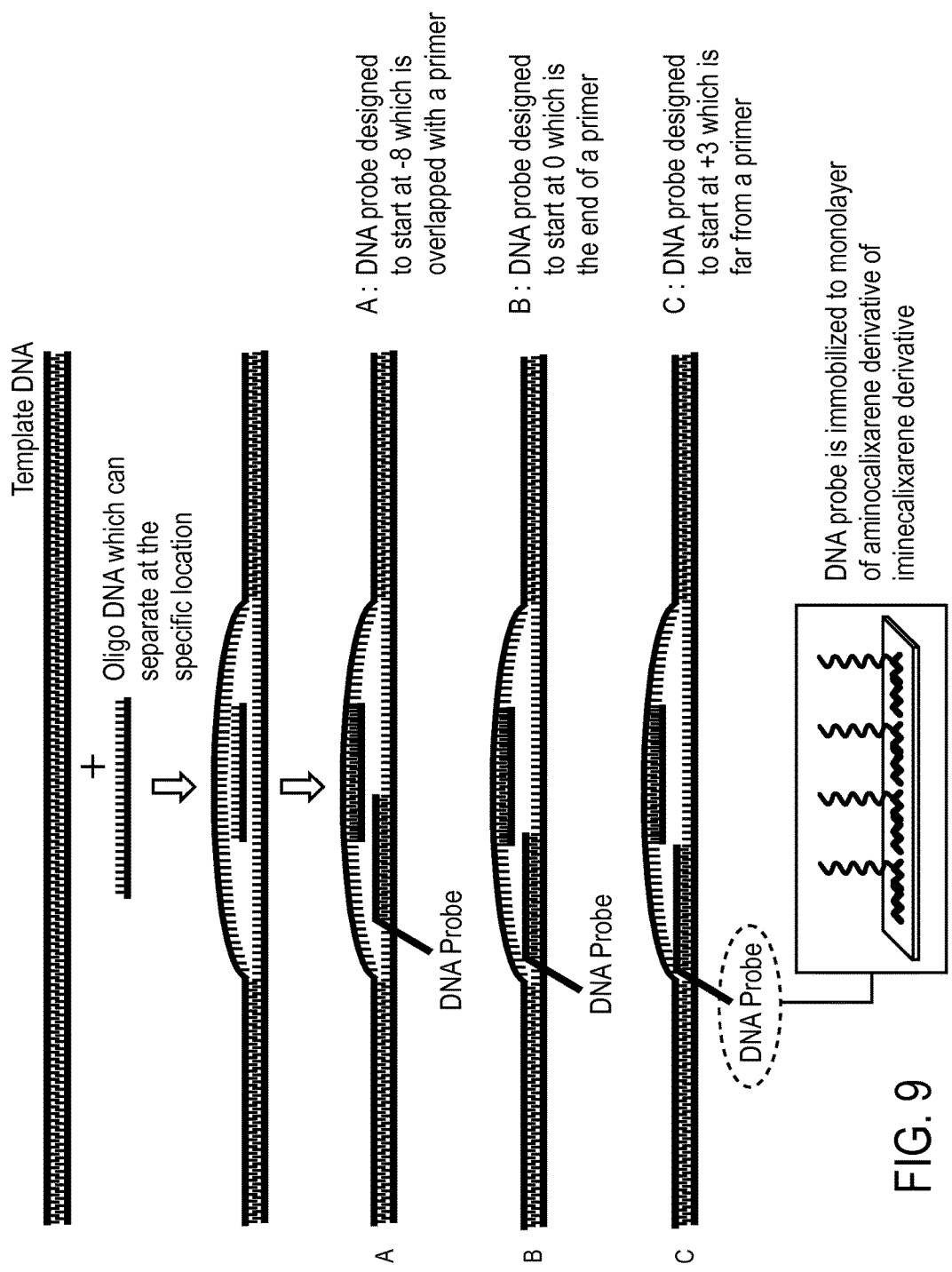
FIG. 9 is a diagram showing a template DNA where the oligo-DNA, which is designed to have sequences corresponded with some of the template, is bonded. In addition, FIG. 9 also shows a probe designed to have 8 sequences overlapped with the oligo-DNA bonded to the template (e.g., designed to start at −8), a probe designed to start at the end of the oligo-DNA, i.e. 0 sequence far from the oligo-DNA (e.g., designed to start at 0), and a probe designed to start 3 sequences far from the oligo-DNA bonded with the template (e.g., designed to start at +3). Each probe was designed to have consecutive guanine bases such that they can be immobilized on the chip prepared according to FIG. 1 and FIG. 2. The thus-prepared DNA chip carries out room-temperature (20° C.~30° C.) hybridization with the template DNA where the oligo-DNA designed to be bonded with the template, with high specificity and sensitivity.

Probes starting at various positions and having various length were designed as shown in FIG. 3 and FIG. 4 and were immbolized on a chip, and then comparison experiments were carried out. By using the results of the experiments, the technology of designing a probe with high sensitivity and specificity as shown in FIG. 8 and FIG. 9 was developed. In addition, the technology of designing an optimal probe and the technology of preparing a DNA chip for carrying out room-temperature hybridization by using the same were developed.

Figures 1, 1A, 2:
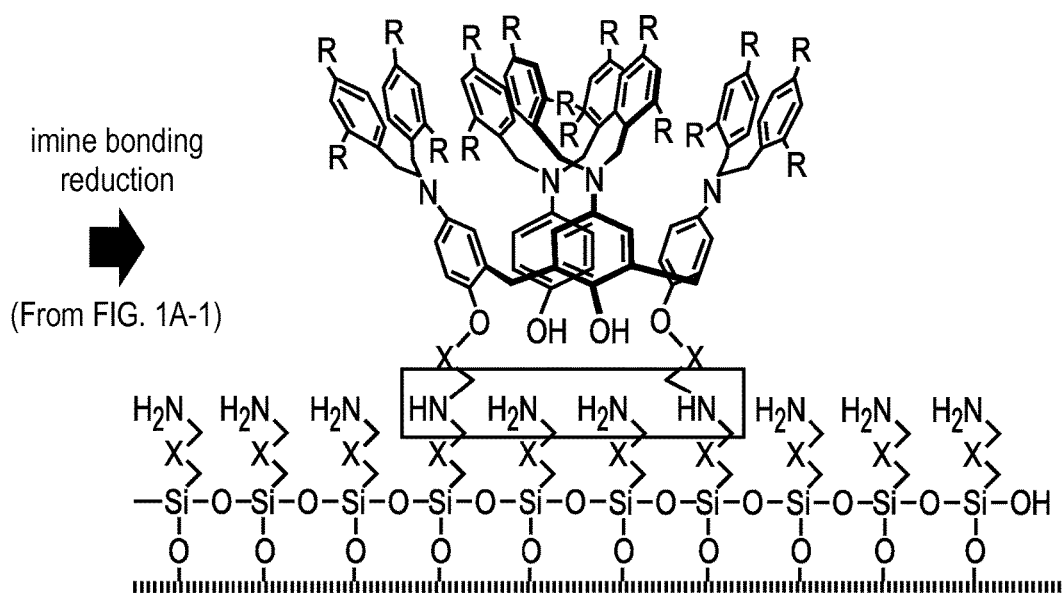
FIG. 2 is a diagram showing the process of preparing a DNA chip by bonding the aminocalixarene derivative or iminecalixarene derivative of FIG. 1 on the surface of a glass substrate where amine functional groups are attached to form a monolayer and then immobilizing a probe oligo-DNA having consecutive guanine bases.
Figure 1B:
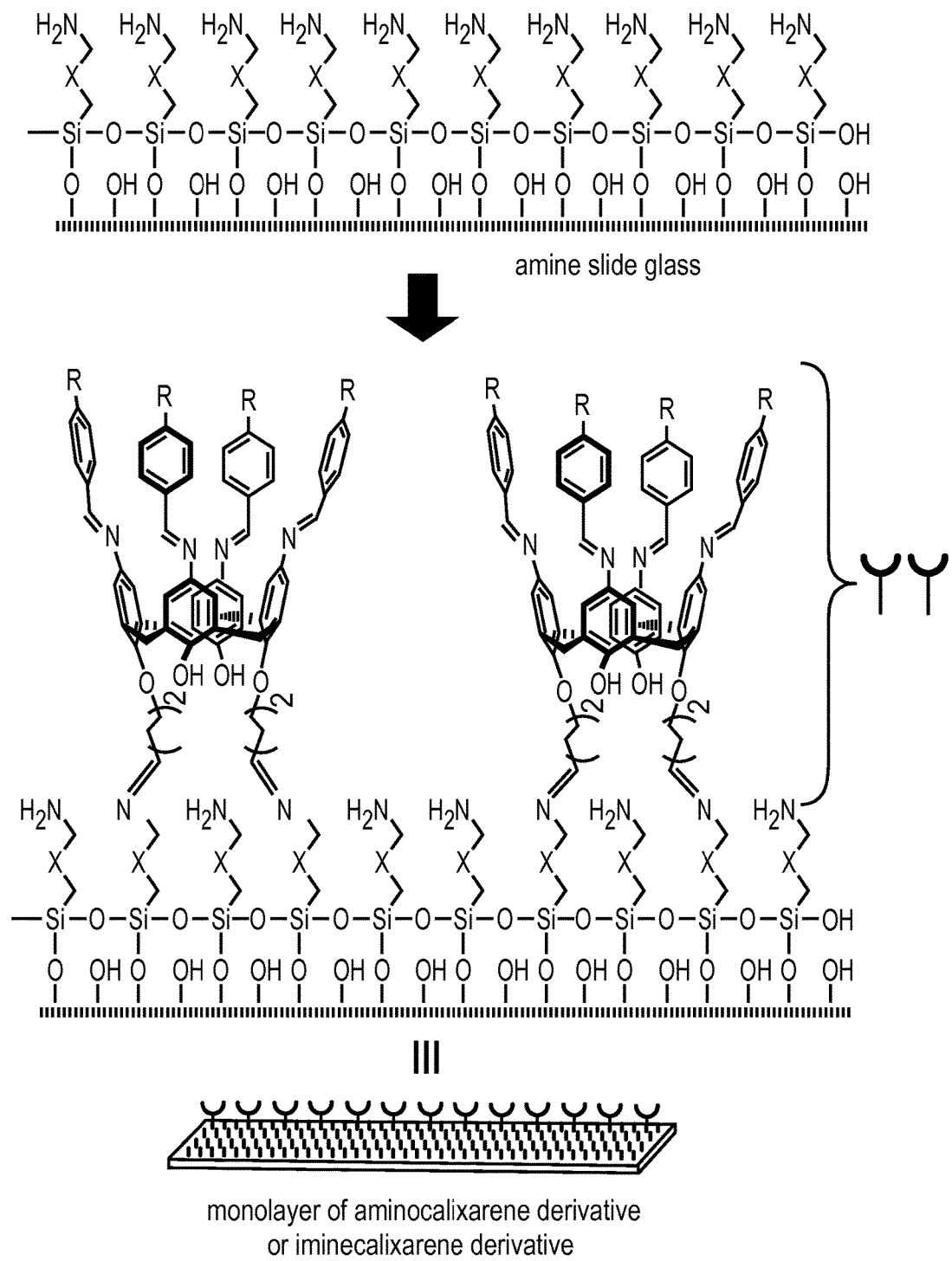
Figure 2:
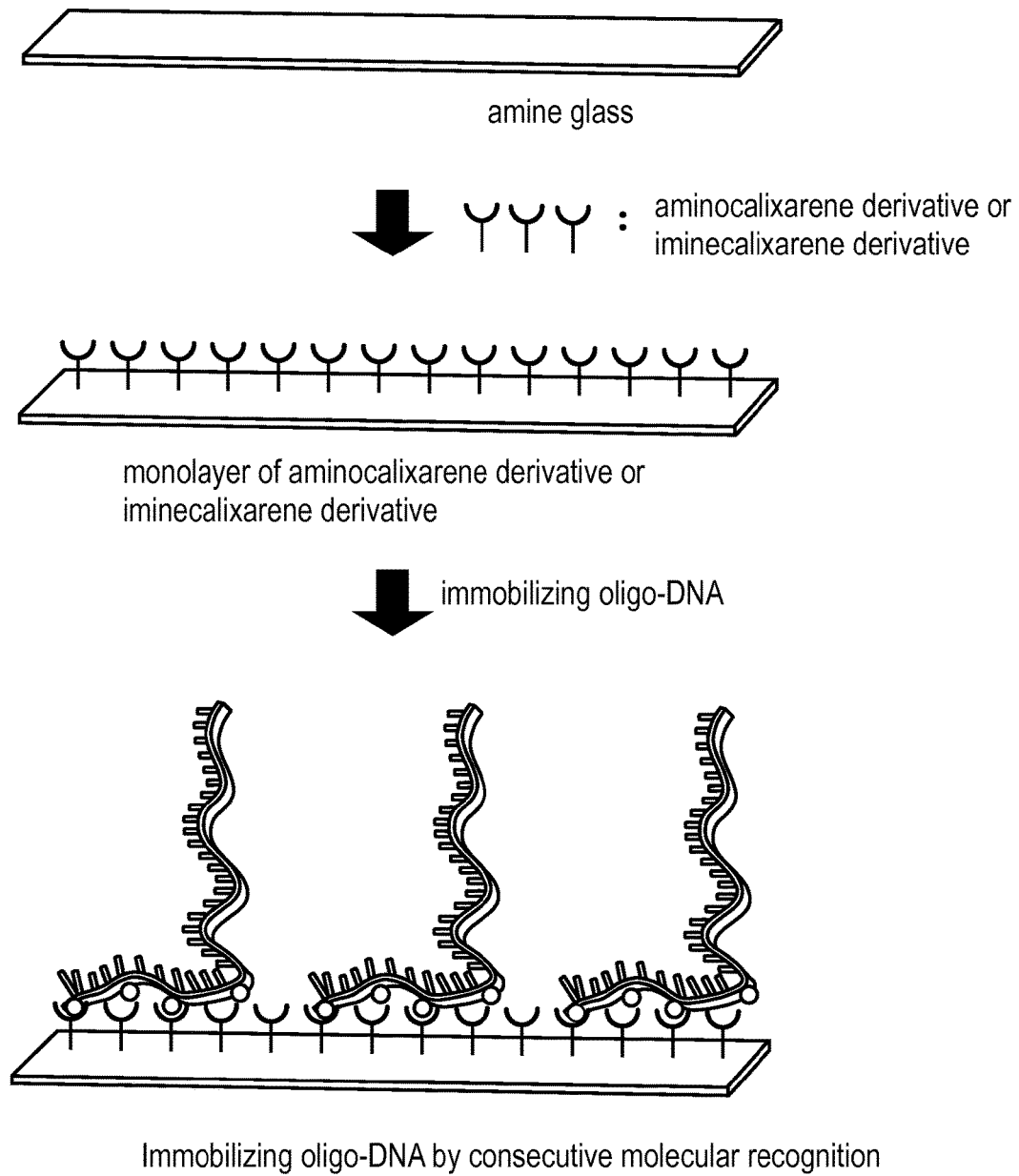

In addition, in order to confirm whether the newly developed technology is applicable to the products on the market, a probe for genotyping HPV capable of carrying out room-temperature hybridization was designed, and then the probe was immobilized according to the method of FIG. 2 to prepare a DNA chip capable of genotyping HPV at a room temperature.

On the thus-prepared DNA chip for genotyping HPV, the PCR product obtained by amplifying a virus template or a standard template of a known genotype using a fluorescence-labeled primer was spreaded at a room temperature, or a large amount of standard templates or virus templates were spreaded directly at a room temperature. Then, it was observed whether said templates exhibit signals when they are complementary to the used probes. FIG. 7 shows the results of the experiment. Through this process, a novel probe and a HPV DNA chip where said probe is immobilized were developed. FIG. 7 shows the results obtained from the DNA chips where the probes designed to achieve excellent results are immobilized.

In the case of using a DNA chip where dozens of types of probes are immobilized, such as a DNA chip for genotyping HPV, etc., even when the causes for nonspecific bonding are almost removed, and even when strong signals are observed at a position corresponding to the spreaded genotype, non-specific signals are observed at a position where no fluorescence should be detected; that is, it is difficult to completely remove nonspecific bonding. Accordingly, the present invention developed new technology of designing a positive control probe which can play a critical role in determining which signal is due to a specific bond made by a complementary genotype and which signal is due to a nonspecific bond as shown in FIG. 5 and FIG. 6. The experimental results of FIG. 7 show that in the case of immobilizing a positive control probe designed according to this technology and then determining whether a signal is a specific signal or a non-specific signal based on the signal of the positive control probe, it is possible to select specific signals only.

Putting together such technology, the present invention achieved new technology of designing a probe capable of carrying out genotyping at a room temperature as shown in FIG. 8 and FIG. 9, technology of preparing a DNA chip where the thus designed probe is immobilized according to the process of FIG. 2, and technology of designing a probe for a positive control which minimizes signals due to non-specific hybridization. FIG. 8 shows the process of an immobilized probe making bonds during room-temperature hybridization.

Based on this technology, the present invention achieved technology of preparing a DNA chip capable of genotyping by carrying out room-temperature hybridization. In addition, the present invention applied this technology to genotyping viruses. That is, the present invention developed a DNA chip for genotyping carrying out room-temperature hybridization (HPV genotyping DNA chip carrying out room-temperature hybridization) by designing a probe for genotyping HPV which can be used for room-temperature (20° C.~30° C.) hybridization according to the method of FIG. 8 and immobilizing the same.

The present application relates to a method of designing a DNA probe chip for room-temperature hybridization, wherein the method comprises designing DNA probe to start at −10~+5 position that is between −10 position which is overlapped 10 sequences with a primer and +5 position which is 5 sequences far from the 3'-terminal of the primer, based on 0 position which is 3'-terminal of the primer.

Preferably, above method comprises designing the DNA probe to start at −8~+3 position. (See FIG. 8 )

Another embodiment of present application provied the DNA probe chip for room-temperature hybridization designed according to the method comprising designing DNA probe to start at −10~+5 position that is between −10 position which is overlapped 10 sequences with a primer and +5 position which is 5 sequences far from the 3'-terminal of the primer, based on 0 position which is 3'-terminal of the primer.

In the preferred embodiment, above DNA probe's length is from 15 mer to 30 mer, preferably from 17 mer to 23 mer.

In another preferred embodiment, 7~15 consecutive guanine bases are further attached on the 5'-terminal of above DNA probe.

In addition, above DNA probe is attached on a Self-assembled monolayer(SAM), wherein the the Sell-assembled monolayer is formed by attaching the aminocalixarene derivative of following formula 1 on the solid substrate selected from the group consisting of amine-modified slide glass, glass fiber, silicon wafer and fused silica:

[formula 1]

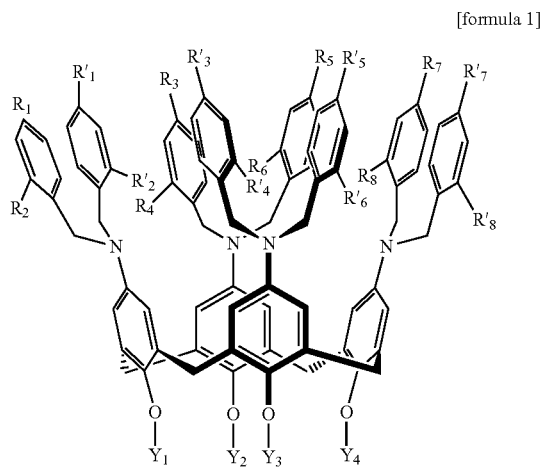

[wherein. $R_1$, $R_2$, $R_3$, $R_4$, $R_5$, $R_6$, $R_7$, $R_8$, $R'_1$, $R'_2$, $R'_3$, $R'_4$, $R'_5$, $R'_6$, $R'_7$ and $R'_8$ are independently selected from the group consisting of —H, —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —$OC_6H_4CH_3$, —$OC_6H_4C(CHhd 3)_3$, —$OC_6H_4CF_3$, —$OC_6H_4Cl$, —$OCOCH_3$, —$NHCOCH_3$, —$CONHCH_3$, —CN, —COOH, and —COOR wherein R represents —$CH_3$ or —$C_2H_5$;

$Y_1$, $Y_2$, $Y_3$ and $Y_4$ are independently selected from the group consisting of —H, —$(CH_2)_n$—CH=O, —$(CH_2)_n$—SH, —$(CH_2CH_2O)_m$—$CH_2CH_2$—CH=O, —$(CH_2CH_2O)_m$—$CH_2CH_2$—SH, —$(CH_2)_m$—$C_6H_4$—$(CH_2)_c$—Z and —CO—$(CH_2)_{m-1}$—$C_6H_4$—$(CH_2)_c$—Z, wherein, n=2~15, m=1~10, c=0~10, Z=—SH, —CHO, —COOH or —$NH_2$, and —$C_6H_4$—and —$C_6H_5$ are defined as phenyl group]; or is formed by attaching the iminecalixarene derivative of following formula 2 on the solid substrate selected from the group consisting of amine-modified slide glass, glass fiber, silicon wafer and fused silica:

[formula 2]

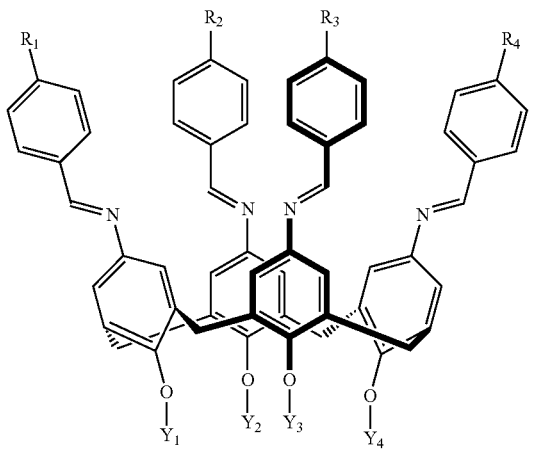

[wherein.

$R_1$, $R_2$, $R_3$ and $R_4$ are independently selected from the group consisting of —H, —$CH_3$, —$C_2H_5$, —$C_3H_7$, —$OCH_3$, —Cl, —$C_6H_5$, —OH, —$OCH_2CH_3$, —Br, —$CF_3$, —$OCH_2C_6H_5$, —$OC_6H_5$, —$OC_6H_4CH_3$, —$OC_6H_4C(CH_3)_3$, —$OC_6H_4Cl$, —$OCOCH_3$, —$NHCOCH_3$, —$CONHCH_3$, —CN, —COOH, and —COOR wherein R represents —$CH_3$ or —$C_2H_5$;

$Y_1$, $Y_2$, $Y_3$ and $Y_4$ are independently selected from the group consisting of —H, —$(CH_2)_m$—CH=O, —$(CH_2)_n$—SH, —$(CH_2CH_2O)_m CH_2$—CH=O, —$(CH_2CH_2O)_m$—$CH_2CH_2$—SH, —$(CH_2)_m$—$C_6H_4$—$(CH_2)_c$—Z and —CO—$(CH_2)_m$—$C_6H_4$—$(CH_2)_c$—Z wherein, n=2~15, m=1~10, c=0~10, Z is a group selected from the group consisting of —SH, —CHO, —COOH and —$NH_2$, and —$C_6H_4$—and —$C_6H_5$ are defined as phenyl group].

In addition, the present application relates to a method of designing a DNA probe chip for room-temperature hybridization, wherein the method comprises designing DNA probe to start at −10~+5 position that is between −10 position which is overlapped 10 sequences with a DNA oligomer and +5 position which is 5 sequences far from the 3'-terminal of the DNA oligomer, based on 0 position which is 3'-terminal of the DNA oligomer having the sequences corresponded with a template DNA. (See FIG. 9)

Preferably, above method comprises designing the DNA probe to start at −8~+3 position.

Another embodiment of present application provied the DNA probe chip for room-temperature hybridization designed according to method comprising designing DNA probe to start at −10~+5 position that is between −10 position which is overlapped 10 sequences with a DNA oligomer and +5 position which is 5 sequences far from the 3'-terminal of the DNA oligomer, based on 0 position which is 3'-terminal of the DNA oligomer having the sequences corresponded with a template DNA.

In the preferred embodiment, above DNA probe's length is from 15 mer to 30 mer, preferably from 17 mer to 23 mer.

In another preferred embodiment, 7~15 consecutive guanine bases are further attached on the 5'-terminal of above DNA probe.

In addition, above DNA probe is attached on a Self-assembled monolayer (SAM), wherein the the Self-assembled monolayer is formed by attaching the aminocalixarene derivative of above formula 1 or formular 2 on the solid substrate selected from the group consisting of amine-modified slide glass, glass fiber, silicon wafer and fused silica.

According to disclosed methods of present application, it may be capable of genotyping (eg. HPV genotyping) which comprises spreading PCR product on the DNA probe chip designed according to the methods and hybridizing at room temperature.

In addition, according to disclosed methods of present application, it may be capable of genotyping (eg. HPV genotyping) which comprises spreading a template DNA attached with 15~30 mer DNA oligomer having the sequences corresponded with the template DNA on the DNA probe chip designed according to the methods and hybridizing at room temperature.

In case of HPV genotyping, the DNA probe has sequence selected from the group consisting of sequence Nos. 30~47 shown in FIG. 4. Furthermore, the DNA probe is attached on a Self-assembled monolayer, and the the Self-assembled monolayer is formed by attaching the aminocalixarene derivative of above formula 1 or formular 2 on the solid substrate selected from the group consisting of amine-modified slide glass, glass fiber, silicon wafer and fused silica.

In addition, the present application provide a DNA probe for positive control or mixture thereof wherein the DNA probe is designed to start at −10~−3 position that is between −10 position which is overlapped 10 sequences with a primer and −3 position which is overlapped 3 sequences with the primer, based on 0 position which is 3'-terminal of the primer. Preferably, above DNA probe for positive control or mixture thereof comprises designing the DNA probe to start at —8~−5 position.

Above DNA probe for positive control or mixture thereof may have sequence selected from the group consisting of sequence Nos. 52, 53, 56 and 60~62, and being used for HPV genotyping.

The present application also provide a method of genotyping which comprises immobilizing above DNA probe for positive control or mixture thereof on a DNA chip having an immobilized DNA probe for genotyping.

Preferably, the present application also provide a DNA probe chip designed according to above methods, wherein the DNA probe chip is designed to allow room-temperature hybridization for genotyping.

Furthermore, the genotyping method may be a spectroscopic method comprising fluorescence spectroscopy or visible light spectroscopy for analyzing the result of measuring the total amount of the bonded genes obtained from spreading DNA or RNA solution on a DNA chip having immobilizing DNA probe.

The DNA chip designed according to present method shows excellent sensitivity with regard to probe, in case of spreading PCR product or template DNA. As such, effect of experiment of present method discloses with description about drawings.

The aminocalixarene derivative of formula 1 and iminecalixarene derivative of formula 2 used in said method for the preparation of a DNA probe chip were prepared by binding macromolecules onto the surface of an amine-modified glass substrate according to the method of FIG. 1. Then, the DNA chip using the probe according to the present invention was prepared by immobilizing consecutive guanine bases on a glass slide according to the method of FIG. 2. The immobilization of the probe according to the present invention was carried out according to the method of immobilizing DNAs according to Example 3.

In order to determine a probe achieving the most excellent results in hybridization, various probes designed to start at various positions were compared through experiments. Probe designing, which performs optimally at a room temperature, is that 17-19 mer probe starts at 0, +3, or +6 position (which is far from the 3'-terminal of a primer used in PCR) as shown in Table 3. And designed probes were immobilized on a DNA chip. Then, the same PCR products were spreaded on said DNA chip. Then, the probes were compared for sensitivity. The results showed that the probes start at −10~+5, preferably −8~+3, more preferably 0~+3 position (based on 0 position as 3'-terminal of a primer) exhibit optimal sensitivity (See FIG. 4, FIG. 8 and Example 5).

Figure 3A:
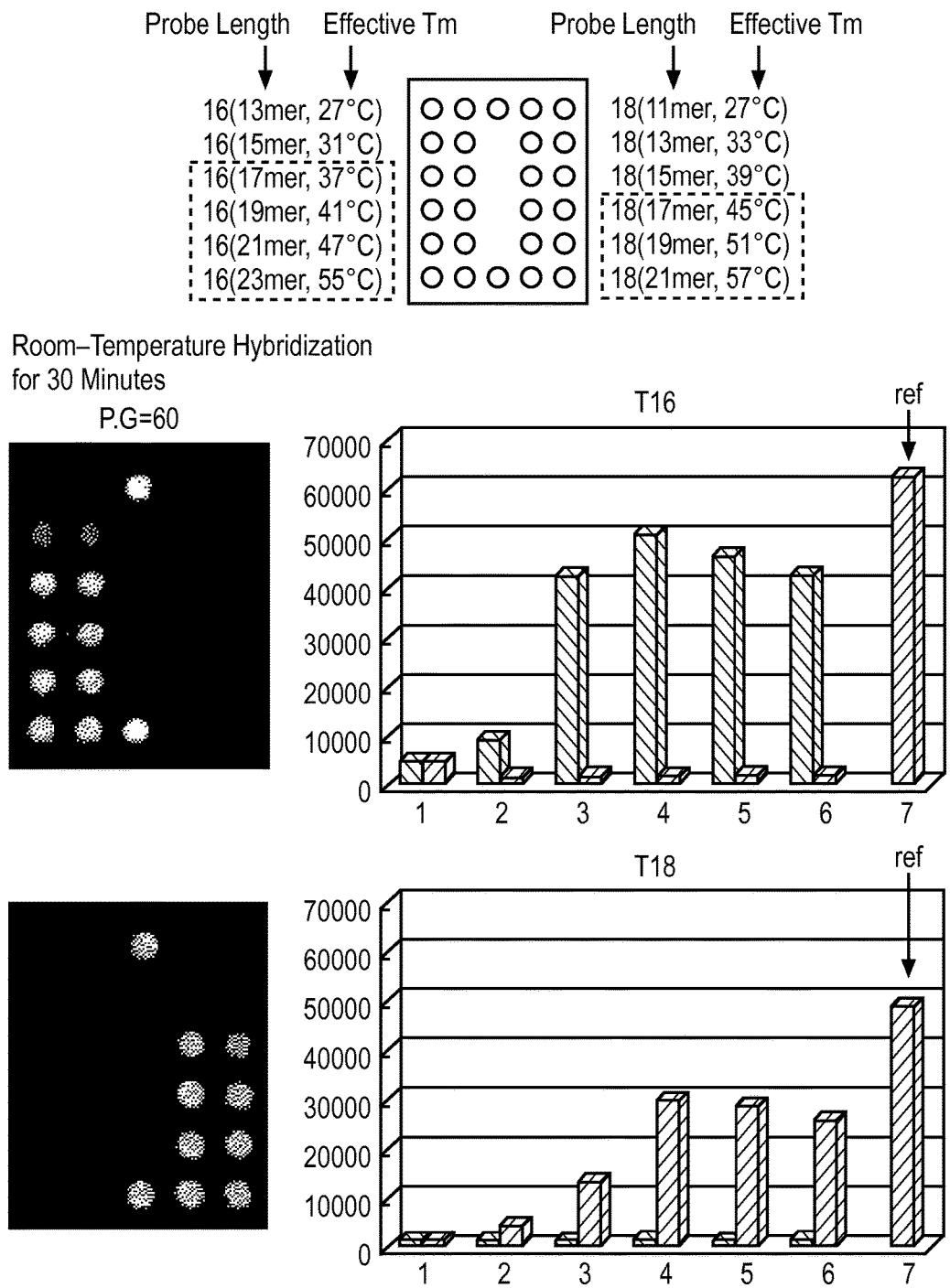
FIG. 3a shows the results of actual experiments carried out repeatedly using the PCR products of standard templates of HPV-16 and HPV-18, which show that, in a probe designing, the probe whose base sequence starts at 0 position and having length of 17 mer to 23 mer shows the most excellent hybridization result.

FIG. 3a shows the results of actual experiments, wherein probes for HPV-16 and HPV-18 designed to start at 0 position, i.e. 0 sequence far from the end of primer as shown in Table 1, and then the probe length which achieves optimal sensitivity was determined. From the results of Examples 3 and 4, it was confirmed that 15~30 mer, preferably 17~23 mer probe has optimal sensitivity.

Figures 2, 3B:
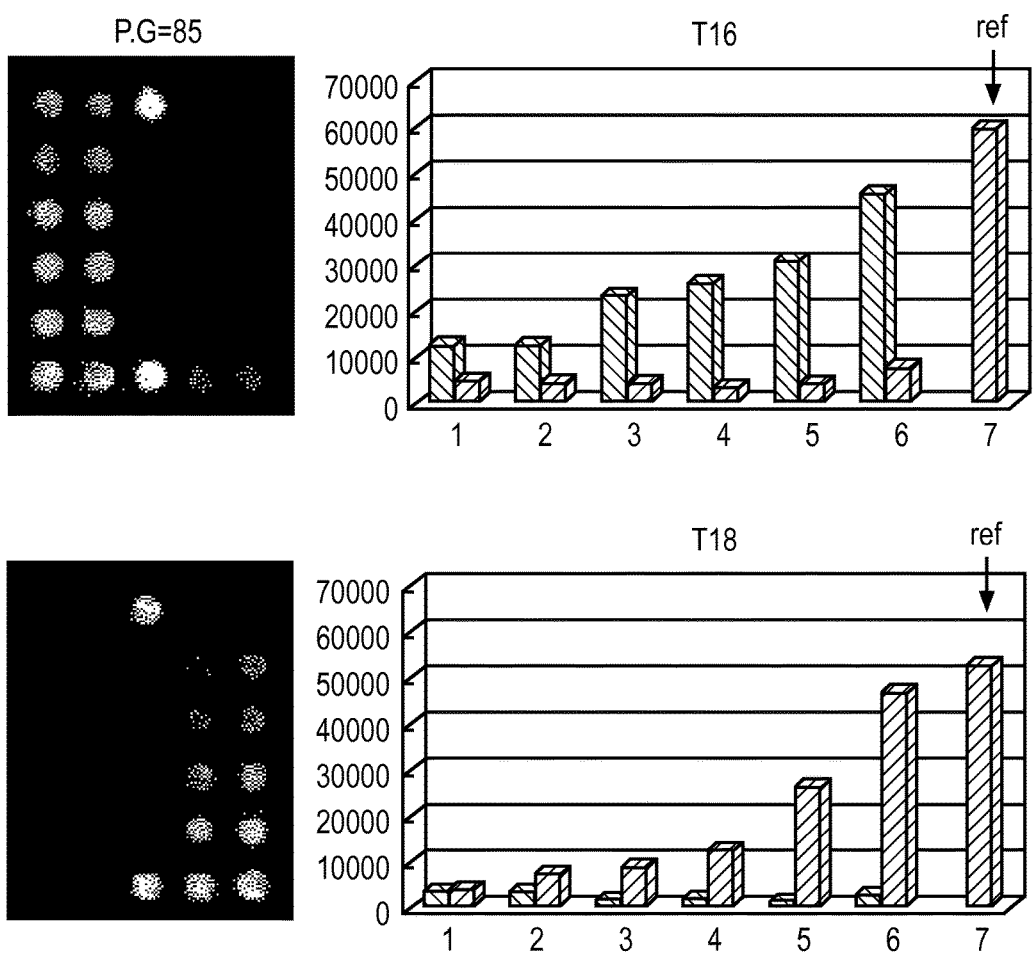
FIG. 3b shows the results of actual experiments, wherein the same amount of PCR products obtained by using the same template were spreaded on a conventional HPV DNA probe chip for high temperature hybridization and a HPV DNA probe chip for room-temperature hybridization, and then genotyping of HPV 16 and HPV 18 was carried out. According to the genotyping results from the two chips, the intensity of signals increased about 50 times in the case of carrying out room temperature hybridization. In addition, in the case of carrying out high-temperature hybridization, the ratio of actual signals to nonspecific signals was about 4~5 times, whereas in the case of room temperature hybridization, the ratio of actual signals to nonspecific signals were about 20 times. That is, the results show that nonspecific bonding was minimized and signals were amplified in the case of carrying out room temperature hybridization.
Figure 4A:
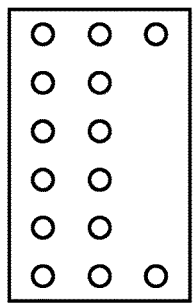
FIG. 4 shows the results of actual experiments showing that an optimum signal level can be obtained in the case of designing a probe to start at 0~+3 position based on the 3'-terminal of primer and to have specific length. Among the probes satisfying said requirements, the probe exhibiting optimum results for each genotype at Tm 37° C.~55° C. was selected. Table 4 describes said probes according to HPV type.
Figure 4A:
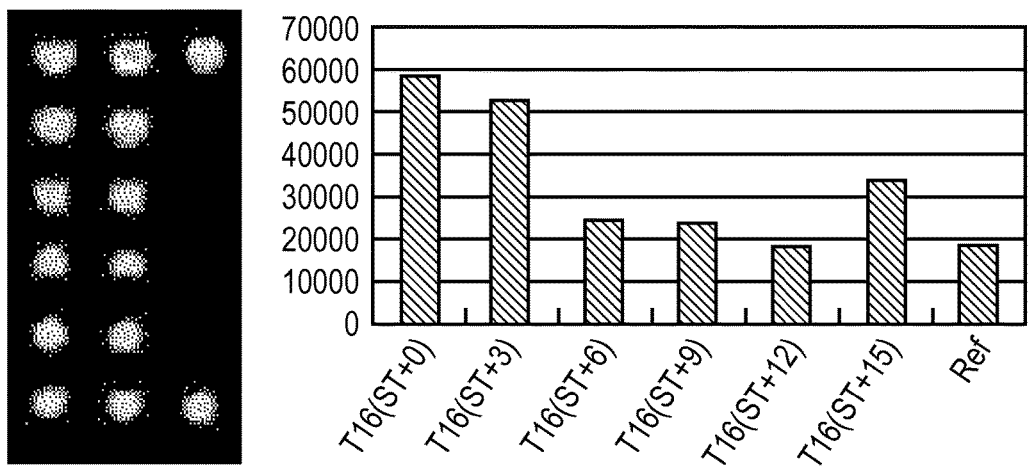
Figure 4A:
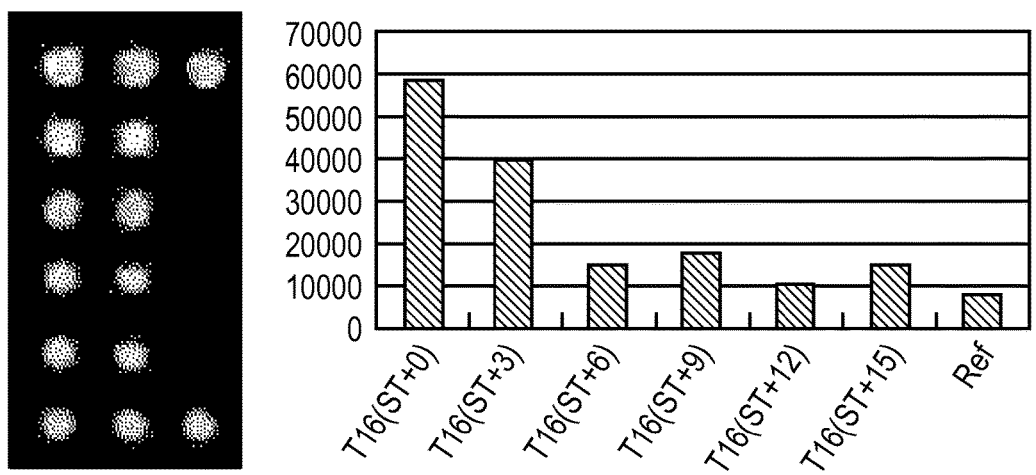
Figure 4B:
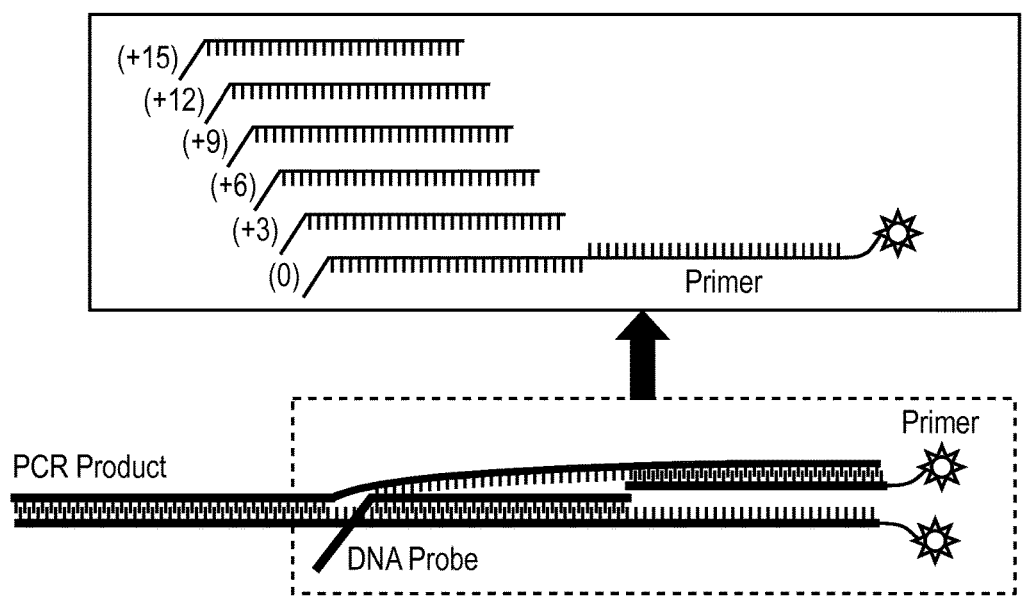

FIG. 3a shows the actual results obtained when spreading the PCR products using standard templates of HPV-16 and HPV-18 at a room temperature on a chip where the designed probes are immobilized. A DNA chip was prepared by designing 12 probes for HPV-16 and HPV-18 situated 0 sequence far from the end of primer and having Tm (melting temperature) values of 27° C.~57° C. as shown in Table 1, and then immobilizing said probes on the chip according to the method of Example 3. On said chip, PCR products obtained by using the templates of HPV-16 and HPV-18 and the primer set of Table 2 were respectively spreaded in the same amount according to the method of Example 4. Then, hybridization was carried out for 30 minutes at a room temperature and 50° C., respectively. The results are shown in FIG. 3b. Comparing the probes having the same Tm value, the sensitivity increased about 50 times at a room temperature. And the ratio of actual signals to nonspecific signals, which shows the specificity, was about 4~5 times at a high temperature, and about 20 times at a room temperature, which shows that the speicificity increased sharply and the sensitivity, e.g., the signal, was amplified. In accordance with the results of FIG. 3 and FIG. 4, the probes exhibiting optimal sensitivity and specificity for 18 types of HPV were selected among the probes having a Tm value of 37° C.~55° C. The base sequence of the probes for each genotype is shown in Table 4.

FIG. 5 illustrates the results of actual experiments and shows the method of determining a positive control and the thus determined positive control. For the PCR product of each genotype, the standard probe for its positive control was designed to have 12 sequences (starting from position first base to twelfth base with respect the the end of a primer) and 5 to 11 overlapping base sequences with the primer (in the case where the base sequence has five overlapping sequences, it was described with −5; in the case where the base sequence has eight overlapping sequences, it was described with −8; and if the base sequence has eleven overlapping sequences, it was described with −11) as shown in FIG. 5. Then, the PCR product of a HPV standard template was spreaded onto a DNA chip where such a standard probe is immobilized, according to the method of Example 7. From the results, it was confirmed that the probe (−5) designed such that 5 mer overlaps with a primer and the probe (−8) designed such that 8 mer overlaps with a primer did not exhibit signals if they are not complementary to the spreaded genotypes. On the other hand, the probe (positive control, −11) designed such that 11 mer overlaps with a primer, is bonded with all types of PCR products or primers to show fluorescence. Therefore, a positive control was designed to have −5~8 mer base sequence.

FIG. 6 shows the process of designing and determining a standard probe, e.g., positive control, to determine a standard for differentiating the signals obtained by specific bonds and non-specific bonds and thereby to carry out precise genotyping. It shows the result of actual experiments carried out in accordance with Example 8, after spreading the PCR product of the template of each genotype on a real area where the probes of the genotypes according to Table 4 are immobilized, and on the area of a positive control on a DNA chip where 20 mer probes candidate (Table 6) obtained by combining the −8 mer base sequence determined in FIG. 5 with the 12 mer probes for each genotype of Table 4 at the 3'-end of the probes. The results expressed by candidate standard probe for positive control are summarized in Table 7. Then, PCR products of specific HPV types were immobilized, and then 6 probes showing signals for the most types of PCR products were selected as candidates for standard probes. Then, mixed standard probes for a positive control on a DNA chip were made by mixing said probes as in Table 8 and immobilizing them.

FIG. 7 shows the results of repeated experiments obtained by spreading the products obtained by PCR amplifying standard templates of each type using the primer set of Table 2 in accordance with example 9, on a HPV genotyping DNA chip for room-temperature hybridization prepared by immobilizing the two mixed types of positive controls determined in FIG. 6, the negative control (position to measure the nonspecificity) of Table 8, a hybridization control (a position where a fluorescence-labeled primer is attached, which identifies whether a consistent amount of PCR product was input) and the DNA probes of 18 HPV types of Table 4. The results show that when using a DNA chip capable of carrying out room-temperature hybridization, fluorescence of each HPV types is observed exactly at a positive control and at positions of the probes of each type, and the amount of spreaded PCR products can be calculated by using the fluorescence intensity of the position of a hybridization control, and that nonspecific bonds are almost removed as compared to a DNA chip carrying out high-temperature hybridization.

In present application, the aminocalixarene derivative of formula 1 and the iminecalixarene derivative of formula 2, a self-assembled monolayer prepared by using the same, and a DNA chip prepared by immobilizing oligo-DNAs on said self-assembled monolayer may be prepared according to the method disclosed in Korean Patent Application Nos. 10-2005-0096322, 10-2005-0103857, 10-2005-0105340 and 10-2005-0110824, which are incorporated herein by reference.

Now, the present invention will be described in further detail with reference to Examples. However, it should be understood that the present invention is by no means restricted to such specific Examples.

EXAMPLE

Example 1

Method of modifying a slide glass where amine functional groups are attached by applying a solution wherein 5,11,17,23-tetrabenzylaminocalix[4] arene-1,3-hexanealdehyde (TDBACAHA) is dissolved

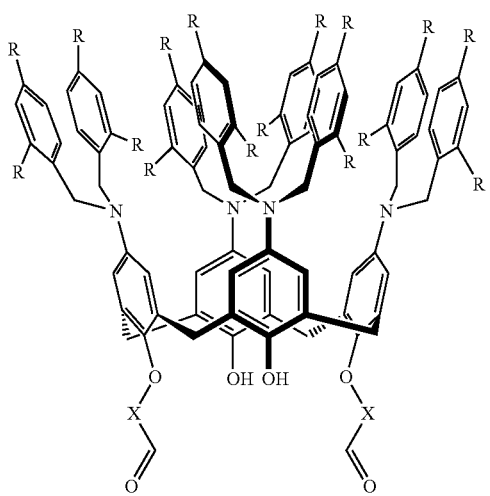

Among the derivatives of formula 1, 0.1-5.0 mM of 5,11,17,23-tetrabenzylaminocalix[4] arene-1,3-hexanealdehyde (TDBACAHA) was dissolved in an organic solvent such as $CHCl_3$ etc. to prepare a solution. As shown in FIG. 1, a slide glass where amine functional groups are attached (e.g., amineglass slide) [prepared according to Langmuir, 1997, Vol 13, pp 4305-4308; Langmuir, 1996, Vol 12, pp 5338-5342] was immersed in the thus-prepared solution for 1~24 hours, and then the slide glass was sequentially washed with chloroform, acetone, and then finally with water, and then dried to form the aminocalixarene monolayer. Another aminocalixarene derivative monolayer was prepared according to the same method. Said glass substrate includes amine-modified slide glass, amine-modified glass fiber, amine-modified silicon wafer and amine-modified fused silica.

Example 2

Method of modifying a slide glass where amine functional groups are attached by applying a solution wherein 5,11,17,23-tetrabenzylaminocalix[4] arenc-1,3-hexancaldehyde (TDBACAHA) is dissolved

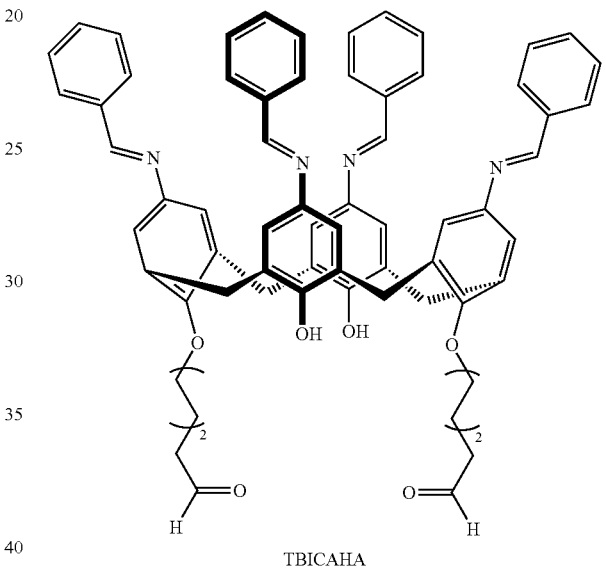

TBICAHA

Among the derivatives of formula 1, 0.1~5.0 mM of 5,11,17,23-tetrabenzylaminocalix[4] arene-1,3-hexanealdehy de (TDBACAI1A) was dissolved in an organic solvent such as $CHCl_3$ etc. to prepare a solution. As shown in FIG. 1, a slide glass where amine functional groups are attached (e.g., amineglass slide) [prepared according to Langmuir, 1997, Vol 13, pp 4305-4308; Langmuir, 1996, Vol 12, pp 5338-53421] was immersed in the thus-prepared solution for 1~24 hours, and then the slide glass was sequentially washed with chloroform, acetone, and then finally with water, and then dried to form the aminocalixarcne monolayer. Another aminocalixarene derivative monolayer was prepared according to the same method. Said glass substrate includes amine-modified slide glass, amine-modified glass fiber, amine-modified silicon wafer and amine-modified fused silica.

Example 3

Method of immobilizing oligo-DNAs to carry out an experiment for determining a useful temperature for hybridization on a DNA chip and a comparison experiment A Genetics microarray device (G.B.) was used for the oligo-DNA immobilization shown in FIG. 2. In order to determine a useful temperature for hybridization on a DNA chip, an immobilization solution was prepared by dissolving 33.75 pmol/µl of oligo-DNAs having 9 consecutive guanine bases in a BMT spotting solution. Said immobilization solution was spreaded at the rate of 1~5 nL by using the Genetics microarray device (G.B.) onto a glass substrate (glass slide) having an aminocalixarene derivative monolayer or an iminecalixarene derivative monolayer as shown in FIG. 1 prepared according to the methods of Examples 1 and 2. Then, oligo-DNAs were immobilized in the form of spots of 150~180 µm in width. After carrying out immobilization for 1~4 hours, the glass slide was washed with 500 ml of BMT Wa-A-1 solution for one minute one time, washed with BMT Wa-A-2 solution 2 times, and then immersed into 250 Ml of BMT blocking solution for 30 minutes in order to block the positions where oligo-DNAs are not immobilized. Then, the glass slide was washed again with 500 ml of BMT Wa-A-1 solution for 3 minutes one time, washed with BMT Wa-A-2 solution 2 times, and then dried.

TABLE 1

| Probe name | Base sequence (5'-3') | Description |
|---|---|---|
| 16-1 | GGG GGG GGG TTA TTT TCC TAC A (Sequence No.1) | 13 mer, 27° C. |
| 16-2 | GGG GGG GGG AA TTA TTT TCC TAC A (Sequence No.2) | 15 mer, 31° C. |
| 16-3 | GGG GGG GGG C AAA TTA TTT TCC TAC A (Sequence No.3) | 17 mer, 37° C. |
| 16-4 | GGG GGG GGG TTC AAA TTA TTT TCC TAC A (Sequence No.4) | 19 mer, 41° C. |
| 16-5 | GGG GGG GGG AG TTC AAA TTA TTT TCC TAC A (Sequence No.5) | 21 mer, 47° C. |
| 16-6 | GGG GGG GGG C CAG TTC AAA TTA TTT TCC TAC A (Sequence No.6) | 23 mer, 55° C. |
| 18-1 | GGG GGG GGG ATT CTC CCT CT (Sequence No.7) | 11 mer, 27° C. |
| 18-2 | GGG GGG GGG GT ATT CTC CCT CT (Sequence No.8) | 13 mer, 33° C. |
| 18-3 | GGG GGG GGG G TGT ATT CTC CCT CT (Sequence No.9) | 15 mer, 39° C. |
| 18-4 | GGG GGG GGG GTG TGT ATT CTC CCT CT (Sequence No.10) | 17 mer, 45° C. |
| 18-5 | GGG GGG GGG CT GTG TGT ATT CTC CCT CT (Sequence No.11) | 19 mer, 51° C. |
| 18-6 | GGG GGG GGG A GCT GTG TGT ATT CTC CCT CT (Sequence No.12) | 21 mer, 57° C. |

Example 4

Method for determining a useful temperature for the hybridization on a DNA chip by using a PCR product and method for a comparison experiment A) PCR Amplification by Using a Synthesized PCR Primer DNA extracted and purified from SiHa cell line (HPV-16, KCLB 30035, Human squamous carcinoma, cervix) and HeLa cell line (HPV-18, KCLB 21550, Human squamous carcinoma, cervix) which were purchased from Korean Cell Line Bank (KCLB) was used as a template DNA. While using the purified DNAs of HPV-16 and HPV-18 as a template and the primers in Table 2, PCR was carried out according to the following method. The primers used for PCR were synthesized by Bionia Co. Ltd. by our order. PCR was carried out by treating a reaction solution purchased from Bionia Co. Ltd., comprising 10 µl of PCR buffer, 1.5mM $MgCl_2$, 250uM dNTP, 30mM KCl, 10mM Tris-HCl (pH9.0), Taq polymerase (1 unit) and 1 µl of primer (10 pmol/µl), 7 µl of distilled water, 1 µl of template DNA, at 94° C. for 5 minutes one time, and then 35 times repeating a treatment at 94° C. for 1 minute, at 45° C. for 45 seconds, and at 72° C. for 1 minute, and then treating the solution at 72° C. for 5 minutes one time. Then, 5 µl of the thus-prepared reaction solution was applied to 2% agarose gel along with a DNA size standard maker, and then it was subjected to electrophoresis. Here, the electrophoresis gel was dyed by 0.00005% ethidium bromide solution. Whether the band emerging on each of the paths in the gel is valid was confirmed by using UV.

TABLE 2

| Primer name | Base sequence (5'- 3') |
|---|---|
| Forward | GATGGTGATATGGTAGATACAGGATTT (Sequence No.13) |
| Cy5-Reverse | Cy5-CCTAGTGGCTCTATGGTAACCTCTGACGC (Sequence NO.14) |

B) Method for Carrying Out Hybridization Using a PCR Product

In order to carry out hybridzation with a fluorescence-labeled target DNA synthesized by PCR according to the above method, 5 µl of fluorescence-labeled target DNA and 55 µl of BMT hyb-mixA were put into a 1.5 µl tube to prepare a mixed solution. Then, the thus-prepared solution was heated in water at 100° C. for 3 minutes, and then cooled on ice for 3 minutes. Then, the 60 µl of mixed solution was injected into a glass slide where a hybridization chamber is attached prepared according to the method of Example 3. Then, one of the glass slides was left in a thermo-hygrostat oven at a temperature of 50° C. for 30 minutes and the other glass slide was left at a room temperature (20~30° C.) for 30 minutes to carry out hybridization. After the hybridization was completed, the glass slides were washed with BMT Wa-B-2 (4xSSC) solution at a room temperature (20~30° C.) for 2 minutes for two times, and then dried. Then, the fluorescence was analyzed quantitatively by using a microarrayer scanner (GSI Lumonics, U.S.A.). Actual results are shown in FIGS. 3a and 3b.

Example 5

Comparison experiment for comparing the detection efficiency of an oligo-DNA chip according to the distance from a primer In order to carry out a comparison experiment for comparing the detection efficiency of an oligo-DNA chip according to the distance from a primer, an immobilization solution was prepared by dissolving 33.75 pmol/µl of 6 types of oligo-DNAs having 9 consecutive guanine bases as shown in FIG. 3 in a BMT spotting solution. Said immobilization solution was spotted in the form as shown in FIG. 4 according to the method of Example 3 by using the Genetics microarray device (G.B.) to prepare a chip.

TABLE 3

| Primer name | Base sequence (5' - 3') | Description |
|---|---|---|
| 16 + 0 | GGG GGG GGG T TCA AAT TAT TTT CCT ACA (Sequence No.15) | 0 mer far from the split site (0 mer) |
| 16 + 3 | GGG GGG GGG C AGT TCA AAT TAT TTT CCT (Sequence No.16) | 3 mer far from the split site (+3 mer) |
| 16 + 6 | GGG GGG GGG GCC AGT TCA AAT TAT TTT (Sequence No.17) | 6 mer far from the split site (+6 mer) |
| 16 + 9 | GGG GGG GGG TTA GCC AGT TCA AAT TAT (Sequence No.18) | 9 mer far from the split site (+9 mer) |
| 16 + 12 | GGG GGG GGG AAT TTA GCC AGT TCA AAT (Sequence No.19) | 12 mer far from the split site (+12 mer) |
| 16 + 15 | GGG GGG GGG CA AAT TTA GCC AGT TCA (Sequence No.20) | 15 mer far from the split site (+15 mer) |

Then, in order to carry out hybridzation with the same fluorescence-labeled target DNA (HPV-16) as that of Example 4, 5 μl of fluorescence-labeled target DNA and 55 μl of BMT hyb-mixA were put into a 1.5 Ml tube to prepare a mixed solution. Then, the thus-prepared solution was heated in water at 100° C. for 3 minutes, and then cooled on ice for 3 minutes. Then, the 60 μl of mixed solution was injected into the glass slide where a hybridization chamber is attached. Then, the glass slide was left in a thermo-hygrostat oven at a room temperature of 20~30° C. for 30 minutes to carry out hybridization. After the hybridization was completed, the glass slide was washed with BMT Wa-B-2 (4×SSC) solution at a room temperature (20~30° C.) for 2 minutes for two times, and then dried. Then, the fluorescence was analyzed quantitatively by using a microarrayer scanner (GSI Lumonics, U.S.A.). Actual results are shown in FIG. 4.

Analyzing fluorescence at each spot (wherein the fluorescence sensitivity was indicated minimum value of 0 and maximum value of 65000), the detection efficiency decreased to about ½~⅓ when the probe is more than 6 mer away from the primer. The fluorescence of +3 mer (52000) was actually at least 2 times than that of +6 mer (25000). Although not indicated in Table 4, the result showed that the fluorescence of +4 mer(GGG GGG GGG CAG TTC AAA TTA TTT TCC) and +5 mer (GGG GGG GGG CCA GTT CAA ATT ATT TTC) was respectively 48000 and 38000, which is about half degree between +3 mer (52000) and +6 mer (25000). According to said result, high detection efficiency of fluorescence showed high value up to +5 mer, compared 6 mer or more than.

Example 6

Selection of a Probe for a HPV Oligonucleotide DNA Chip

A) Design of a HPV Oligonucleotide Probe

Oligo nucleotide capable of being used as a type-specific probe which can selectively bond with oncogenic HPV DNA, which is closely related to cervical cancer, was designed. First, the whole DNA base sequences of a total of 72 HPV types (e.g., HPV-1a, -2a, -3, -4, -5, -6b, -7, -8, -9, -10, -11, -12, -13, -15, -16, -16r, -17, -18, -19, -20, -21, -22, -23, -24, -25, -26, -27, -28, -29, -30, -31, -32, -33, -34, -35, -35h, -36, -37, -38, -39, -40, -41, -42, -44, -45, -47, -48, -49, -50, -51, -52, -53, -54, -55, -56, -57, -58, -59, -60, -61, -63, -65, -66, -67, -68, -70, -72, -73, -74, -76, -77, -80) were obtained from NCBI (National Center for Biotechnology Information) of U.S.A. and the HPV database in Los Alamos National Laboratory. Among the obtained DNA sequences, type-specific base sequences for each genotype were selected. Then, based on the results of Examples 3, 4 and 5, a probe with high specificity was designed.

B) Selection from the Designed Probes and Synthesis

Probes which can specifically bond with a high risk group of HPVs having a high probability of causing cancer. e.g., HPV-16, -18, -31, -33, -35, -45, -51, -56, -58, -59, -66, -68, -39, and a low risk group of oncogenic HPVs, e.g., HPV-6, -11, -34, -40, -42, were selected with priority, among the 72 types of HPVs obtained from the design process. The Sequence number and type of DNA probe discloses in Table 4.

TABLE 4

| Base sequence (5' - 3') | HPV type |
|---|---|
| GGG GGG GGG T TCA AAT TAT TTT CCT ACA (Sequence No.30) | HPV-16 |
| GGG GGG GGG GT GTG TAT TCT CCC TCT (Sequence No.31) | HPV-18 |
| GGG GGG GGG AGT ACA TAC TTT CCT ACA (Sequence No.32) | HPV-31 |
| GGG GGG GGG GT GCT TTT TTT CCC ACT (Sequence No.33) | HPV-33 |
| GGG GGG GGG T ACT AGT TAT TTT CCT ACT (Sequence No.34) | HPV-35 |
| GGG GGG GGG T GTG TAT TCC CCT TCT (Sequence No.35) | HPV-45 |
| GGG GGG GGG TAT ATA TAC TCT GCT ACT (Sequence No.36) | HPV-51 |
| GGG GGG GGG AGA GAA CCC CCT CCG AGT (Sequence No.37) | HPV-56 |
| GGG GGG GGG GT GCA TTT TTT CCA ACT (Sequence No.38) | HPV-58 |
| GGG GGG GGG CC AAC CCA GGC AGT TAT TTA (Sequence No.39) | HPV-59 |
| GGG GGG GGG T CCT CCC AGT TCT GTA (Sequence No.40) | HPV-66 |
| GGG GGG GGG GTG TAT GCC CCC TCG CC (Sequence No.41) | HPV-68 |
| GGG GGG GGG CT GTA TAC TGC CCC TCT (Sequence No.42) | HPV-39 |

TABLE 4-continued

| Base sequence (5' - 3') | HPV type |
|---|---|
| GGG GGG GGG AGG CAG TAT TTA TTA CTC CAC (Sequence No.43) | HPV-40 |
| GGG GGG GGG AGT ATA TAT GTT AAC ACC (Sequence No.44) | HPV-6 |
| GGG GGG GGG TCT GTA GCT ACT AGT ATT TAT GTA CAT ACA (Sequence No.45) | HPV-11 |
| GGG GGG GGG GT GTG TTT TAT CCT ACT (Sequence No.46) | HPV-34 |
| GGG GGG GGG CA GAC ATA ATT TAG GTA GTA GTA (Sequence No.47) | HPV-42 |

Example 7

Experiment for Determining a Positive Control by Determining the Number of the Bases by Using a Common Amplified Region Probes were designed in order to comprise 12 mer from a primer (12 mer toward the 5'-terminal from the end of a primer) which have HPV type-specificity and base sequences gradually extended by 3 mer from −5 mer for each probe extended, up to 29 mer length, and then immobilized. Then, in order to carry out an experiment for determining the length of a positive control by using a common amplified region whose specificity is not influenced by primer using the PCR product of HPV-16 and HPV-18, a chip was prepared by spotting 10 types of oligo-DNAs related to HPV-16 and having 9 consecutive guanine bases as shown in Table 5 according to the method of Example 3.

TABLE 5

| Probe name | Base sequence (5' - 3') | Description |
|---|---|---|
| 16 + 0 | GGG GGG GGG T TCA AAT TAT TTT CCT ACA (Sequence No.15) | Located 0 mer from the split site (0 mer) |
| 12 + 5 mer | GGG GGG GGG TAT TTT CCT ACA CCT AG (Sequence No.21) | 17 mer general sequence (−5 mer) |
| 12 + 8 mer | GGG GGG GGG TAT TTT CCT ACA CCT AGT GG (Sequence No.22) | 20 mer general sequence (−8 mer) |
| 12 + 11 mer | GGG GGG GGG TAT TTT CCT ACA CCT AGT GGT TC (Sequence No.23) | 23 mer general sequence (−11 mer) |
| 12 + 14 mer | GGG GGG GGG TAT TTT CCT ACA CCT AGT GGT TCT AT (Sequence No.24) | 26 mer general sequence (−14 mer) |
| 12 + 17 mer | GGG GGG GGG TAT TTT CCT ACA CCT AGT GGT TCT ATG GT (Sequence No.25) | 29 mer general sequence (−17 mer) |
| 12 + 20 mer | GGG GGG GGG TAT TTT CCT ACA CCT AGT GGT TCT ATG GTT AC (Sequence No.26) | 32 mer general sequence (−20 mer) |

TABLE 5-continued

| Probe name | Base sequence (5' - 3') | Description |
|---|---|---|
| 12 + 23 mer | GGG GGG GGG TAT TTT CCT ACA CCT AGT GGT TCT ATG GTT ACC TC (Sequence No.27) | 35 mer general sequence (−23 mer) |
| 12 + 26 mer | GGG GGG GGG TAT TTT CCT ACA CCT AGT GGT TCT ATG GTT ACC TCT GA (Sequence No.28) | 38 mer general sequence (−26 mer) |
| 12 + 29 mer | GGG GGG GGG TAT TTT CCT ACA CCT AGT GGT TCT ATG GTT ACC TCT GAT GC (Sequence No.29) | 41 mer general sequence (−29 mer) |

In order to carry out hybridization with the same fluorescence-labeled target DNA (HPV-16 and HPV-18) as that of Example 4, 5 μl of target DNAs and 55 μl of BMT hyb-mixA were put into a 1.5 Ml tube to prepare a mixed solution. The mixed solution was heated in water at 100° C. for 3 minutes, and then cooled on ice for 3 minutes. Then 60 μl of the mixed solution was injected into a glass slide where a hybridization chamber is attached. The glass slide was placed in a thermo-hygrostat oven at 25° C. for 30 minutes to carry out hybridization. After the hybridization was completed, the glass slide was washed with BMT Wa-B-2 solution (4×SSC) at a room temperature (25° C.) for two minutes for two times, and then dried. Then the fluorescence intensity was analyzed quantitatively by using a mircoarrayer scanner (GSI Lumonics, U.S.A.). Analyzing fluorescence sensitivity shown in FIG. 5, −5 mer~−29 mer when attached 16 type probe was all detected to have maximum fluorescence of about 65000, whereas when attached 18 type probe was detected to have fluorescence of about 65000 at −11 mer and fluorescence of about 3000 at −8 mer, thus primer used in PCR or comprised in PCR product was not bonded to it. Therefore, the result showed that even if used same primer base sequence as −8 mer, there was rare possibility to express non-specified fluorescence by spreading different PCR product. In this result, the length of positive control that may show hybridization process by bonding to PCR product was determined to have −5 mer~−8 mer. Minus(−) 11 mer which have possibility to bond non-specifically to PCT product because of long length of primer, was excluded.

Also in experiment using −9 mer (GGG GGG GGG TAT TTT CCT ACA CCT AGT GGT) of HPV-16 which is 1 mer longer than −8 mer and −10 mer (GGG GGG GGG TAT TTT CCT ACA CCT AGT GGT T) which is 2 mer longer than −8 mer, fluorescence of HPV-16 was 65000 and that of HPV-18 was 3000, which was neglectable, when the hybridization with fluorescence-labeled target DNA same as Example 4 was carried. Thus, the result confirmed that PCR product of type 16 could be bonded specifically up to −10 mer without non-specificity. If PCR process of HPV-16 had not proceeded, HPV-16 and HPV-18 showed same result in accordance with common sequence according to length of primer. From the result of differentiating between two, in case of the PCR products of HPV-16 template were in the presence, −10 mer, specifically −8 mer of probe could hybridize with them. Thus up to −10 mer of probe is useful to confirm specific genotype is emplified by PCR. Therefore, putting together such result, the experiment showed that specific probe length has specificity PCR product of each virous type, immunity to labeled-primer and selectivity expressing of each type.

Example 8

Experiment for Determining a Positive Control by Using a Common Amplified Region A) Probe Immobilization for Determining a Positive Control In order to determine a positive control for the 18 types of HPVs selected in Example 6, probes consisting of the sequences which can selectively bond with the HPV types were suggested as shown in Table 6. Then, the probes were immobilized on a glass slide, as shown in FIG. 6. Then, probes showing specificity for HPV types were selected. Immobilization of probes were carried out according to the method of Example 3.

TABLE 6

| Probe name | Base sequence (5' - 3') | Description |
|---|---|---|
| PC16 | GGG GGG GGG TAT TTT CCT ACA CCT AGT GG (Sequence No.48) | Positive, 20 mer |
| PC18 | GGG GGG GGG TAT TCT CCC TCT CCT AGT GG (Sequence No.49) | Positive, 20 mer |
| PC31 | GGG GGG GGG TAC TTT CCT ACA CCT AGT GG (Sequence No.50) | Positive, 20 mer |
| PC33 | GGG GGG GGG TTT TTT CCC ACT CCT AGT GG (Sequence No.51) | Positive, 20 mer |
| PC35 | GGG GGG GGG TAT TTT CCT ACT CCT AGT GG (Sequence No.52) | Positive, 20 mer |
| PC45 | GGG GGG GGG TAT TCC CCT TCT CCT AGT GG (Sequence No.53) | Positive, 20 mer |
| PC51 | GGG GGG GGG TAC TCT GCT ACT CCT AGT GG (Sequence No.54) | Positive, 20 mer |
| PC53 | GGG GGG GGG TAT GTT GCT ACA CCT AGT GG (Sequence No.55) | Positive, 20 mer |
| PC56 | GGG GGG GGG TAT GTT GCT ACG CCT AGT GG (Sequence No.56) | Positive, 20 mer |
| PC58 | GGG GGG GGG TTT TTT CCA ACT CCT AGT GG (Sequence No.57) | Positive, 20 mer |
| PC59 | GGG GGG GGG TAT TCC CCT TCC CCT AGT GG (Sequence No.58) | Positive, 20 mer |
| PC66 | GGG GGG GGG TAT GTT GCT ACT CCT AGT GG (Sequence No.59) | Positive, 20 mer |
| PC68 | GGG GGG GGG TAT GCC CCC TCG CCT AGT GG (Sequence No.60) | Positive, 20 mer |

TABLE 6-continued

| Probe name | Base sequence (5' - 3') | Description |
|---|---|---|
| PC6 | GGG GGG GGG TAT GTT AAC ACC CCT AGT GG (Sequence No.61) | Positive, 20 mer |
| PC11 | GGG GGG GGG TAT GTA CAT ACA CCT AGT GG (Sequence No.62) | Positive, 20 mer |
| PC34 | GGG GGG GGG TTT TAT CCT ACT CCT AGT GG (Sequence No.63) | Positive, 20 mer |
| PC42 | GGG GGG GGG TAT TAT CCT ACC CCT AGT GG (Sequence No.64) | Positive, 20 mer |
| PC70 | GGG GGG GGG TAT TCC CCT TCC CCT AGT GG (Sequence No.65) | Positive, 20 mer |

B) Sampling of DNA from a Cell and Amplification of HPV DNA by PCR

Cervical cells were sampled from cervix by using a brush for sampling cervical cells and then put into a 15 ml tube where 5 ml of a preserve solution (PBS) is contained. Then, the solution was intensely agitated for 2 minutes such that the cells stuck to the brush can be dissolved into the preserve solution. Then, the solution was centrifuged at 3000 g for 10 minutes. Then, the cells were precipitated and supernatants were removed. The cells were transferred to a 1.5 ml centrifugal tube by using a serum separtion tube, and then 100 μl of cell lysis buffer (10 mM Tris-HCl, 50 mM KCl, 2.5 mM $MgCl_{2, 0.5}$% Tween 20, 200 ul/ul proteinase K, pH 8.3) was added thereto. The solution was heated in a thermostat at 55° C. for 2 hours. Then, it was further heated at 95° C. and for 10 minutes to deactivate proteinase K. Using the DNA sampled and purified according to the above method as a template DNA and using the primer of Table 2, PCR was carried out according to the following method. The primers used in the PCR was synthesized by Bionia Co. Ltd. by our order. PCR was carried out by treating a reaction solution purchased from Bionia Co. Ltd., comprising 10 μl of PCR buffer, 1.5 mM $MgCl_{2, 250}$ uM dNTP, 30 mM KCl, 10 mM Tris-HCl (pH 9.0), Taq polymerase (1 unit) 1 μl of primer (10 pmol/μl), 7 μl of distilled water, 1 μl of template DNA, at 94° C. for 5 minutes one time, and then 35 times repeating a treatment at 94° C. for 1 minute, at 45° C. for 45 seconds, and at 72° C. for 1 minute, and then treating the solution at 72° C. for 5 minutes one time. Then, 5 μl of the thus-prepared reaction solution was applied to 2% agarose gel along with a DNA size standard maker, and then it was subjected to electrophoresis. Here, the electrophoresis gel was dyed by 0.00005% ethidium bromide solution. Whether the band emerging on each of the paths in the gel is valid was confirmed by using UV.

C) Method of Hybridization Using a PCR Product

In order to carry out hybridization with fluorescence-labeled target DNA, 5 μl of target DNAs and 55 μl of BMT hyb-mixA were put into a 1.5 μl tube to prepare a mixed solution. The mixed solution was heated in water at 100° C. for 3 minutes, and then cooled on ice for 3 minutes. Then 60 μl of the mixed solution was injected into a glass slide where a hybridization chamber is attached. The glass slide was subjected to hybridization at a room temperature (20° C.~30° C.) for 30 minutes. After the hybridization was completed, the glass slide was washed with BMT Wa-B-2 solution (4×SSC) at a room temperature (25° C.) for two minutes for two times, and then dried. Then the fluorescence intensity was analyzed quantitatively by using a mircoarrayer scanner (GSI Lumonics, U.S.A.). The results are shown in FIG. 6. When the PCR product of each HPV type was spreaded, the HPV types described in Table 7 were detected by PC probes. The results of Table 7 show that 4 types of probes including PC 35, PC 45, PC 56, PC 68 can be used as a positive control for HPV-16, -18, -31, -33, -35, -45, -51, -56, -58, -59, -66, -68, -39, -40, -34, and -42, and PC 6 and PC 11 can be used as a positive control for HPV-6 and -11. In addition, the results show that in the case of using PC 1 obtained by mixing PC 35, PC 45, PC 56 and PC 68 and using PC 2 obtained by mixing PC 6 and PC 11, it can be confirmed whether PCR of 18 types of HPVs carried by using the two positive controls.

TABLE 7

| Probe name | HPV types detected |
|---|---|
| PC16 | 16, 31, 35, 42 |
| PC18 | 18, 45 |
| PC31 | 16, 31, 35, 42 |
| PC33 | 33, 35, 58 |
| PC35 | 16, 31, 33, 35, 58, 66, 34, 42 |
| PC45 | 18, 45, 59, 70, 66 |
| PC51 | 31, 33, 35, 51, 56, 58, 66, 34, 53 |
| PC53 | 16, 31, 66, 53, 56 |
| PC56 | 51, 56, 66, 53 |
| PC58 | 33, 34, 35 |
| PC59 | 45, 59, 70 |
| PC66 | 35, 51, 5658, 66, 34, 53 |
| PC68 | 18, 45, 59, 68, 70, 56 |
| PC6 | 6 |
| PC11 | 11 |
| PC34 | 16, 31, 33, 35, 51, 58, 66, 34, 42 |
| PC42 | 34, 42 |
| PC70 | 45, 59, 70 |

Example 9

Experiment for Designing Oligo-DNA Chip, Confirmation by Using PCR Product and Analyzing Template DNA Directly without PCR A) Preparation of HPV Oligonucleotide DNA Chip An HPV oligo-DNA chip was prepared by spotting the 18 types of HPVs (Table 4) selected in Example 6, the 2 positive controls selected in Example 8, 1 hybridization control and 1 negative control (Table 8), in the form as shown in FIG. 7 according to the method of Example 3.

TABLE 8

| Probe name | Base sequence (5' - 3') | Description |
|---|---|---|
| HC | GGG GGG GGG TTT ACA CCT AGT GGC TCT ATG GTG TCC TCT | Hybridization control |
| NC | GGG GGG GGG AAA GCT GCT GCT CGT CGT CGT CGT | Negative control |
| PC1 | PC35: PC45: PC56: PC68 (each mixed in the ratio of 25%) | Positive control |
| PC2 | PC6: PC11:NC (mixed in the ratio of 25%:25%:50%) | Positive control |

TABLE 8-continued

| Probe name | Base sequence (5' - 3') | Description |
|---|---|---|
| PC35 | GGG GGG GGG TAT TTT CCT ACT CCT AGT GG (Sequence No.52) | Positive, 20 mer |
| PC45 | GGG GGG GGG TAT TCC CCT TCT CCT AGT GG (Sequence No.53) | Positive, 20 mer |
| PC56 | GGG GGG GGG TAT GTT GCT ACG CCT AGT GG (Sequence No.56) | Positive, 20 mer |
| PC68 | GGG GGG GGG TAT GCC CCC TCG CCT ACT GG (Sequence No.60) | Positive, 20 mer |
| PC6 | GGG GGG GGG TAT GTT AAC ACC CCT AGT GG (Sequence No.61) | Positive, 20 mer |
| PC11 | GGG GGG GGG TAT GTA CAT ACA CCT AGT GG (Sequence No.62) | Positive, 20 mer |

B) Experiment for Identifying HPV Genotypes by Using a PCR Product

Cervical cells were sampled from cervix by using a brush for sampling cervical cells and then put into a 15 ml tube where 5 ml of reserve solution (PBS) is contained. Then, the solution was intensely agitated for 2 minutes such that the cells stuck to the brush can be dissolved into the reserve solution. Then, it was centrifuged at 300 g for 10 minutes. Then, the cells were precipated and supernatants were removed. The cells were transferred to a 1.5 ml centrifugal tube by using a serum separtion tube, and then 100 µl of cell lysis buffer (10 mM Tris-HCl, 50 mM KCl, 2.5 mM Mg Cl$_2$ $_{,\ 0.5}$% Tween 20, 200 ul/ul proteinase K, pH 8.3) was added thereto. The solution was heated in a thermostat at 55° C. for 2 hours. Then, it was further heated at 95° C. and for 10 minutes to deactivate proteinase K. Using the DNA extracted and purified according to the above method as a template DNA, a chip was spreaded according to the method of Example 8 to obtain results. FIG. 7 shows the photos obtained after carrying out room-temperature hybridization using the 18 sets of modified probes synthesized in the present invention and the analysis results thereof. In each drawing, PC 1 and PC 2 are positive controls and HC is a control to confirm whether hybridization occurred. As can be clearly seen from the drawing, hybridization occurred in the region where the probe complementary to the spreaded HPV type is spotted, PC and in HC only, and nonspecific hybridization did not occur.

C) Preparation of Template DNA Sample in Order to Confirmation Experiment without PCR Directly Cervical cells were sampled from cervix by using a brush for sampling cervical cells and then put into a 15 ml tube where 5 ml of reserve solution (PBS) is contained. Then, the solution was intensely agitated for 2 minutes such that the cells stuck to the brush can be dissolved into the reserve solution. Then, it was centrifuged at 3000 g for 10 minutes. Then, the cells were precipated and supernatants were removed. The cells were transferred to a 1.5 ml centrifugal tube by using a serum separtion tube, and then 100 µl of cell lysis buffer (10 mM Tris-HCl, 50 mM KCl, 2.5 mM Mg Cl$_2$ $_{,\ 0.5}$% Tween 20, 200 ul/ul proteinase K, pH 8.3) was added thereto. The solution was heated in a thermostat at 55°

C. for 2 hours. Then, it was further heated at 95° C. and for 10 minutes to deactivate proteinase K. After purifying the extracted template DNA by using Binding column of Bionia co. Ltd., then was dissolved by 50 µl of elute solution to prepare template DNA. The purified template DNA was analyzed quantitatively by using Spectrophotometer (instrument: Nanodrop of Nanodrop co.). Following FIG. 9 showed the result of analyzing prified DNA by Spectrophotometer.

TABLE 9

| HPV type | Measurement (1st) (ng/µl) | Measurement (2nd) (ng/µl) | Measurement (3rd) (ng/µl) | Measurement (4th) (ng/µl) |
|---|---|---|---|---|
| Type 16 | 80.1 | 79.8 | 83.5 | 81.1 |

Figure 10:
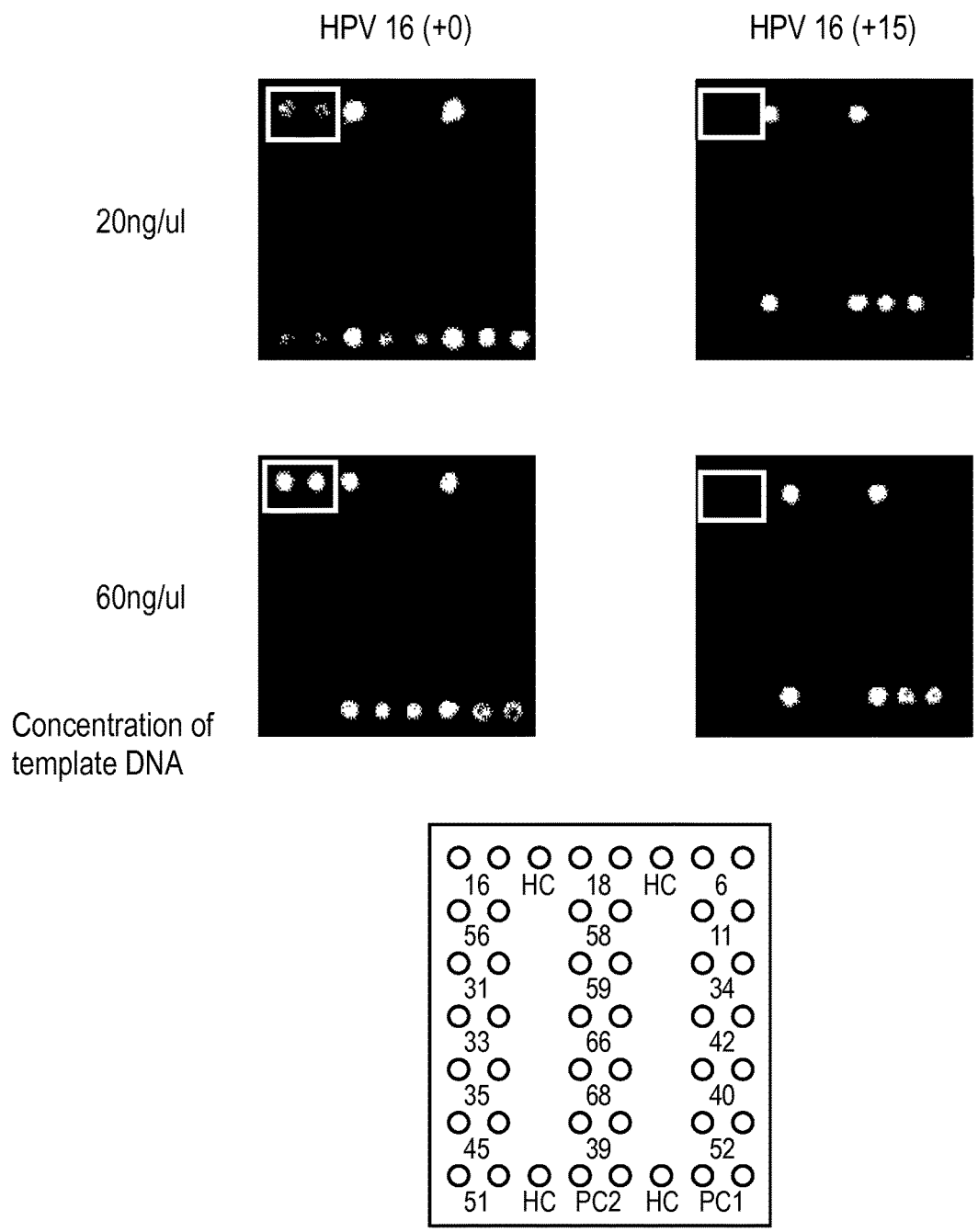
FIG. 10 show the result of fluorescence scanning obtained by directly hybridizing DNA chip with template DNA not treated by PCR process, wherein the template DNA of HPV type 16 is bonded to fluorescence-labeled DNA oligomer, then the template DNA spreaded onto the chip, on which the −8 mer, 0 mer and +15 mer probe DNA is immobilized.

D) Experiment for identifying HPV genotypes by directly using template DNA without PCR process In order to detecting fluorescence by hybridization with extracted template DNA directly, 6 pmol/µl of fluorescence-labeled DNA oligomer (Cy-5-reverse: Cy 5-CCTAGTG-GCTCTATGGTAACCTCTGACGC) (SEQ ID NO. 14) 1 µl was mixed with 18 µl solutions of template DNA prepared according to example 9(c) which were diluted to concentration of 20 ng/µl and 60 ng/µl respectively, and 41 µl of BMT hyb-mixA, in 1.5 ml tube to prepare 60 µl reaction solution. The mixed solution was kept at 94° C. for 45 minutes and 45° C. for 1 hour, and then cooled on ice for 3 minutes. Then 60 µl of the mixed solution was injected into a glass slide prepared according to example 9(a), where a hybridization chamber is attached. The glass slide was subjected to hybridization at a room temperature (20° C.~30° C.) for 1 hour. After the hybridization was completed, the glass slide was washed with BMT Wa-B-2 solution (4×SSC) at a room temperature (25° C.) for two minutes for two times, and then dried. Then the fluorescence intensity was analyzed quantitatively by using a mircoarrayer scanner (GSI Lumonics, U.S.A.). FIG. 10 showed that results of experiment for DNA concentration level enough to ananlyze and efficiency of genotyping according to design DNA probe.

When reaction solution comprising 60 ng/µl concentration of template DNA was spreaded, the fluorescence intensity of HC spot was 65000 and fluorescence intensity of HPV-16 probe position was 42000, that is designed to start at 0 position based on the end of 3'-terminal of the primer as (B) in FIG. 9. And fluorescence intensity of PC 1 spot that is designed to start at −8 position as (A) in FIG. 9 was 61000. In case of the other spots, it was confirmed that the fluorescence intensity decreased less than 5000. When reaction solution comprising 20 ng/µl concentration of template DNA was spreaded, the fluorescence intensity of HC spot was 65000 and fluorescence intensity of HPV-16 probe position was 10000 (0 position). And fluorescence intensity of PC 1 spot (−8) was 57000. In case of the other spots, it was confirmed that the fluorescence intensity decreased at least 2000.

In addition to above result, in case that template DNA of concentration 60 ng/µl was spreaded onto DNA chip on that a probe designed to start at 15 position such as sequence No. 20 is immobilized, it was confirmed that no fluorescence intensity was detected.

Said result showed that the DNA designed to start at the end of primer (0~−8 mer) was detectable without PCR amplification up to 20 ng/µl of concentration. And the result showed, in case that the DNA probe which is designed to start at position far from a primer or fluorescence-labelled DNA oligomer (+15 mer), the fluorescence intensity decreased surprisingly. Thus, when hybridization carried using PCR product, in case of the probe is overlapped with primer (−8 mer) or DNA oligomer, or is closer them (0 mer), the fluorescence intensity increased remarkably.

Compared to the result of example 7, hybridization, by using +5 mer~−10 mer probe with fluorescence-labelled DNA oligomer, and template DNA directly, proceeded higher efficiency than conventional probe.

The composition of the solutions used for the immobilization, washing, etc. of Examples 3~9 is as follows.

BMT spotting solution (4×SSC, 15% glycerol, 1×PBS)

BMT Wa-A-1 (2×SSC, 0.1% SDS)

BMT Wa-A-2 (0.1×SSC)

BMT blocking solution (5% milk casein aqueous solution)

BMT hyb-mixA (4×SSC, 0.01% SDS, 25% formamide, 1×PBS)

BMT Wa-B-1 (4×SSC, 0.1% SDS)

BMT Wa-B-2 (4×SSC)

INDUSTRIAL APPLICABILITY

The present invention developed technology of designing a probe essential for room-temperature (20° C.~30° C.) hybridization, a DNA chip obtained by immobilizing the thus designed probe, and technology of designing a probe for a positive control to be used as a standard for identifying genotypes. In addition, the present invention developed a standard for identifying genotypes by using a mixture of positive control probes. In addition, the present invention developed technology of designing a probe for genotyping HPV and technology of designing and preparing a DNA chip for genotyping HPV prepared by immobilizing the thus designed probe The world's first DNA chip utilizing room-temperature hybridization according to the present invention remarkably solves the sensitivity and specificity problem of existing DNA chips. In addition, by using said technology of designing a probe, the present invention newly developed 18 types of probes for genotyping HPV and technology of designing a standard probe for a positive control to be used as a standard in analyzing a designed probe DNA group and results from a DNA chip. In addition, by applying the above technology, the present invention developed a DNA chip for genotyping HPV carrying out room-temperature hybridization and technology of preparing the same, and thereby developed technology for carrying out genotyping at a room temperature precisely and rapidly. As a result, the present invention designed and prepared world's first DNA chip operating at a room temperature.

What is claimed is:

1. A method of forming a DNA chip for a room-temperature hybridization, the DNA chip comprising a solid substrate, a self-assembled monolayer (SAM) formed on the solid substrate and a probe DNA attached on the SAM, for genotyping a Human Papillomavirus (HPV), wherein the method comprises:

forming a DNA probe to start at one position between −10 position and +5 position of a DNA template that is between a −10 position which is overlapped 10 nucleotides with a primer DNA and a +5 position which is 5 nucleotides far from the 3'-terminal of the primer DNA, based on 0 position which is 3'-terminal of the primer DNA specifically binding to a template DNA for the HPV of interest; and immobilizing the DNA probe on the self-assembled monolayer (SAM) formed on the solid substrate, and wherein the HPV of interest is selected from the group consisting of HPV-6, HPV-11, HPV-16, HPV-18, HPV-31, HPV-33, HPV-34, HPV-35, HPV-42, HPV-45, HPV-51, HPV-53, HPV-56, HPV-58, HPV-59, HPV-66, HPV-68 and HPV-70, wherein the DNA probe has a length of 29 mer, wherein the solid substrate is a glass slide, wherein the DNA probe comprises an artificial sequence selected from the group consisting of SEQ ID NO. 52, SEQ ID NO. 53, SEQ ID NO. 56, SEQ ID NO. 60, SEQ ID NO. 61 and SEQ ID NO. 62, and wherein the self-assembled monolayer is formed by attaching an aminocalixarene derivative as set forth in formula 1 or an iminecalixarene derivative as set forth in formula 2 on the solid substrate:

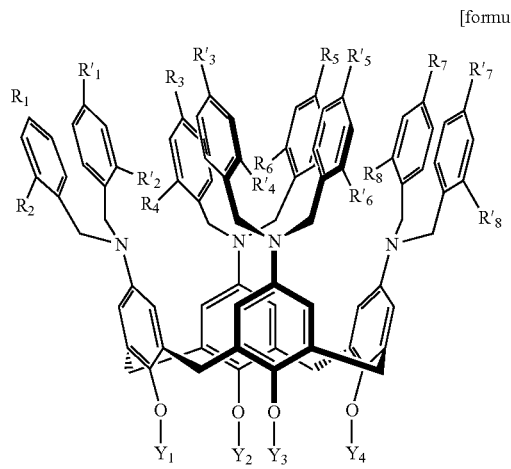

[formula 1]

wherein, $R_1$, $R_2$, $R_3$, $R_4$, $R_5$, $R_6$, $R_7$, $R_8$, $R'_1$, $R'_2$, $R'_3$, $R'_4$, $R'_5$, $R'_6$, $R'_7$ and $R'_8$ are —H; and $Y_1$, $Y_2$, $Y_3$ and $Y_4$ are independently selected from the group consisting of —H and —(CH$_2$)$_n$—CH=O, wherein, n=2-15;

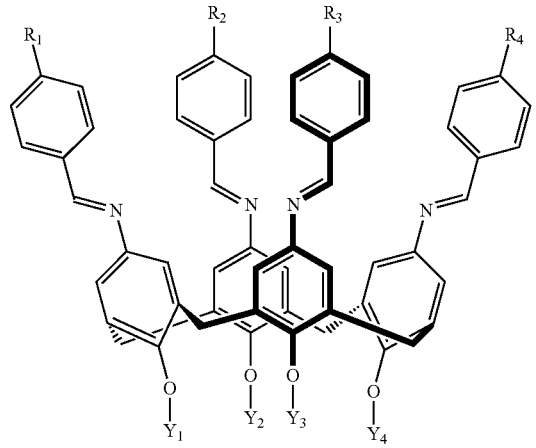

[formula 2]

wherein, $R_1$, $R_2$, $R_3$ and $R_4$ are —H; and $Y_1$, $Y_2$, $Y_3$ and $Y_4$ are independently selected from the group consisting of —H and —(CH$_2$)$_n$—CH=O, wherein, n=2-15.

2. The method of claim 1, wherein the method comprises forming the DNA probe to start at one position between −8 position and +3 position of the template DNA.

3. The method of claim 1, wherein the Self-assembled monolayer is formed by attaching the aminocalixarene derivative of following formula 1 on the solid substrate selected from the group consisting of amine-modified slide glass, glass fiber, silicon wafer and fused silica:

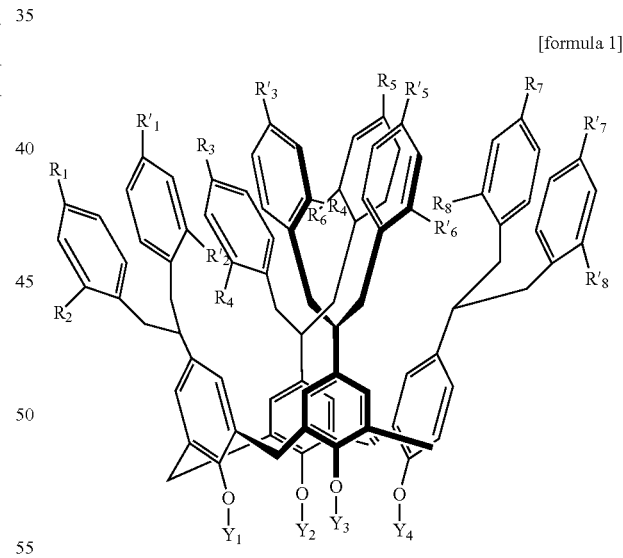

[formula 1]

[wherein, $R_1$, $R_2$, $R_3$, $R_4$, $R_5$, $R_6$, $R_7$, $R_8$, $R'_1$, $R'_2$, $R'_3$, $R'_4$, $R'_5$, $R'_6$, $R'_7$ and $R'_8$ are —H;

$Y_1$, $Y_2$, $Y_3$ and $Y_4$ are independently selected from the group consisting of —H and —(CH$_2$)$_n$—CH=O, wherein, n=2-15].

4. The method of claim 1, wherein the Self-assembled monolayer is formed by attaching the iminecalixarene derivative of following formula 2 on the solid substrate selected from the group consisting of amine-modified slide glass, glass fiber, silicon wafer and fused silica:

[formula 2]
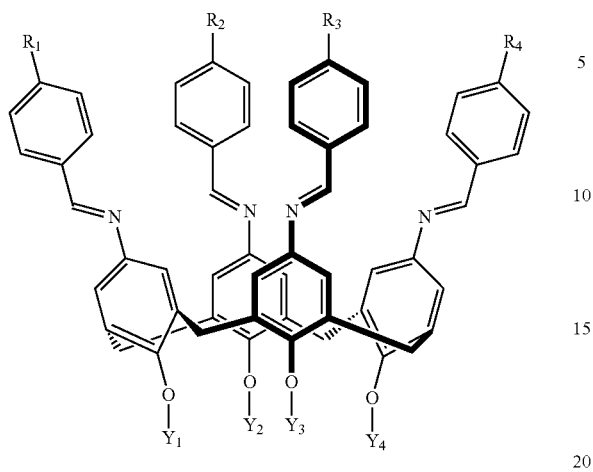
[wherein,
$R_1$, $R_2$, $R_3$ and $R_4$ are —H;
$Y_1$, $Y_2$, $Y_3$ and $Y_4$ are independently selected from the group consisting of —H and —$(CH_2)_n$—CH=O, wherein, n=2-15].
\* \* \* \* \*